United States Patent
Umezaki et al.

(10) Patent No.: US 10,240,122 B2
(45) Date of Patent: Mar. 26, 2019

(54) ACTIVE-ESTER-GROUP-CONTAINING COMPOSITION FOR PRODUCING FIBERS, AND CELL CULTURE SCAFFOLD MATERIAL USING FIBERS PRODUCED FROM ACTIVE-ESTER-GROUP-CONTAINING COMPOSITION

(71) Applicants: NISSAN CHEMICAL INDUSTRIES, LTD., Tokyo (JP); KYOTO UNIVERSITY, Kyoto-shi, Kyoto (JP)

(72) Inventors: Makiko Umezaki, Toyama (JP); Takahiro Kishioka, Toyama (JP); Taito Nishino, Shiraoka (JP); Ayako Otani, Shiraoka (JP); Kenichiro Kamei, Kyoto (JP); Li Liu, Kyoto (JP); Yong Chen, Kyoto (JP)

(73) Assignees: NISSAN CHEMICAL INDUSTRIES, LTD., Tokyo (JP); KYOTO UNIVERSITY, Kyoto (JP)

( * ) Notice: Subject to any disclaimer, the term of this patent is extended or adjusted under 35 U.S.C. 154(b) by 250 days.

(21) Appl. No.: 15/118,481

(22) PCT Filed: Feb. 13, 2015

(86) PCT No.: PCT/JP2015/053890
§ 371 (c)(1),
(2) Date: Aug. 11, 2016

(87) PCT Pub. No.: WO2015/122478
PCT Pub. Date: Aug. 20, 2015

(65) Prior Publication Data
US 2017/0044491 A1   Feb. 16, 2017

(30) Foreign Application Priority Data
Feb. 14, 2014  (JP) .................................. 2014-027044

(51) Int. Cl.
    *C12N 5/00*   (2006.01)
    *D04H 1/728*  (2012.01)
    (Continued)

(52) U.S. Cl.
    CPC ............ *C12N 5/0068* (2013.01); *C08L 33/06* (2013.01); *C08L 33/12* (2013.01); *C08L 33/14* (2013.01);
    (Continued)

(58) Field of Classification Search
    None
    See application file for complete search history.

(56) References Cited

U.S. PATENT DOCUMENTS 5,266,476 A   11/1993  Sussman et al.
8,362,144 B2   1/2013  Martin et al.
(Continued)

FOREIGN PATENT DOCUMENTS

CN   101410508 A   4/2009
CN   101443053 A   5/2009
(Continued)

OTHER PUBLICATIONS

Chinese Patent Office, The First Office Action in Chinese Patent Application No. 201580008422.6 (dated Jun. 28, 2017).
(Continued)

*Primary Examiner* — Erma C Cameron
(74) *Attorney, Agent, or Firm* — Leydig, Voit & Mayer, Ltd.

(57) ABSTRACT

A composition for producing a fiber, containing (A) a polymer compound containing a unit structure represented by the formula (1) and a unit structure represented by the formula (2), (B) a crosslinking agent, (C) an acid compound, and (D) a solvent (Continued)

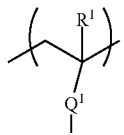

(1)

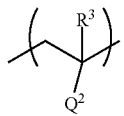

(2)

wherein each symbol in the formulas (1) and (2) is as described in the DESCRIPTION.

10 Claims, 6 Drawing Sheets

(51) Int. Cl.
| | |
|---|---|
| D01D 5/00 | (2006.01) |
| D01F 1/10 | (2006.01) |
| D01F 6/52 | (2006.01) |
| C08L 33/12 | (2006.01) |
| C08L 33/14 | (2006.01) |
| D01F 6/36 | (2006.01) |
| D04H 1/4291 | (2012.01) |
| C08L 33/06 | (2006.01) |

(52) U.S. Cl.
CPC ............... *D01D 5/003* (2013.01); *D01F 1/10* (2013.01); *D01F 6/36* (2013.01); *D01F 6/52* (2013.01); *D04H 1/4291* (2013.01); *D04H 1/728* (2013.01); *C08L 2201/56* (2013.01); *C08L 2203/12* (2013.01); *C12N 2533/40* (2013.01); *C12N 2537/00* (2013.01); *D10B 2509/00* (2013.01)

(56) References Cited

U.S. PATENT DOCUMENTS

| | | |
|---|---|---|
| 2006/0134050 A1 | 6/2006 | Griffith et al. |
| 2009/0047740 A1* | 2/2009 | Elisseeff ............... C12N 5/0068 435/396 |
| 2009/0076530 A1 | 3/2009 | Fukutomi et al. |
| 2010/0168832 A1 | 7/2010 | Neuenschwander |
| 2010/0285094 A1 | 11/2010 | Gupta |
| 2012/0251925 A1 | 10/2012 | Sasaki |
| 2013/0157367 A1 | 6/2013 | Ono et al. |
| 2018/0010115 A1* | 1/2018 | Umezaki ............... C12N 11/08 |

FOREIGN PATENT DOCUMENTS

| | | |
|---|---|---|
| CN | 101466416 A | 6/2009 |
| CN | 101500508 A | 8/2009 |
| CN | 101507661 A | 8/2009 |
| CN | 102274545 A | 12/2011 |
| CN | 102652192 A | 8/2012 |
| CN | 103154338 A | 6/2013 |
| JP | 62-122586 A | 6/1987 |
| JP | 62-502936 A | 11/1987 |
| JP | 2003-265593 A | 9/2003 |
| JP | 2005-060570 A | 3/2005 |
| JP | 2007-325543 A | 12/2007 |
| JP | 2012-052271 A | 3/2012 |
| WO | WO 1986/005811 A | 10/1986 |
| WO | WO 2007/090102 A2 | 8/2007 |
| WO | WO 2007/146261 A2 | 12/2007 |
| WO | WO 2014/210546 A1 | 12/2014 |
| WO | WO 2016/068270 A1 | 5/2016 |
| WO | WO 2011/070893 A1 | 6/2016 |

OTHER PUBLICATIONS

Yanjarappa et al., "Synthesis of Copolymers Containing an Active Ester of Methacrylic Acid by RAFT: Controlled Molecular Weight Scaffolds for Biofunctionalization," *Biomacromolecules,* 7(5): 1665-1670 (2006).

Intellectual Property Office of Singapore, Written Opinion in Singaporean Patent Application No. 11201606729X (dated Jun. 2, 2017).

Kakwere et al., "Orthogonal 'Relay' Reactions for Designing Functionalized Soft Nanoparticles," *J. Am. Chem. Soc.,* 131(5): 1889-1895 (2009).

European Patent Office, Extended European Search Report in European Patent Application No. 15749372.7 (dated Sep. 25, 2017).

Li et al., *Biomaterials,* 26: 5158-5166 (2005).

Ma et al., *Tissue Engineering,* 11(7/8): 1149-1158 (2005).

Wang et al., *Journal of Biomedical Materials Research A,* 100A: 794-801 (2012).

Zhang et al., *Cytotechnology,* 64: 701-710 (2012).

Japanese Patent Office, International Search Report in International Patent Application No. PCT/JP2015/053890 (dated Apr. 28, 2015).

\* cited by examiner

ACTIVE-ESTER-GROUP-CONTAINING COMPOSITION FOR PRODUCING FIBERS, AND CELL CULTURE SCAFFOLD MATERIAL USING FIBERS PRODUCED FROM ACTIVE-ESTER-GROUP-CONTAINING COMPOSITION

CROSS-REFERENCE TO RELATED APPLICATIONS

This patent application is the U.S. national phase of International Patent Application No. PCT/JP2015/053890, filed on Feb. 13, 2015, which claims the benefit of Japanese Patent Application No. 2014-027044, filed Feb. 14, 2014, the disclosures of which are incorporated herein by reference in their entireties for all purposes.

TECHNICAL FIELD

The present invention relates to a composition for producing a fiber, which comprises a polymer compound having an active ester group and a hydroxy group in a side chain, a crosslinking agent, an acid compound, and a solvent, a fiber superior in organic solvent resistance, which is obtained by spinning (preferably, further heating) the composition, and a cell culture scaffold material using the fiber.

BACKGROUND ART

In the bone marrow and basal lamina in the body, cells grow and proliferate in an extracellular matrix constituted of a fiber-like structure of a nano level such as collagen and the like. To provide cells necessary for cell medicine and regenerative medicine, a scaffold material for cell culture that enables efficient culture of cells ex vivo is desired. It is preferable that such cell culture scaffold material mimic as much as possible the in vivo environment surrounding the cell.

It has conventionally been studied to process matrix constituent materials such as collagen and the like extracted from the body into a gel or sponge-like structure and use same as a culture scaffold when cells are cultured ex vivo (see patent document 1). However, these substances derived from living organisms and mainly composed of protein are associated with problems of inability to stand sterilization treatments with autoclave, γ-ray and the like, stability during long-term preservation before use, physical strength, form stability and the like. In addition, since these substances derived from living organisms such as collagen and the like are generally extracted from animals such as cow, pig and the like, a risk of introduction of an infectious substance from these animals is present.

Therefore, studies of structures such as foam, gel, fiber and the like produced using synthetic polymers as materials instead of substances extracted from living organisms, which are used as a culture scaffold, are recently ongoing (see patent document 2-patent document 5). Particularly, application of a synthetic polymer including N-hydroxysuccinimide (NHS) acrylate ester monomer, hydrophilic monomer, and a crosslinking agent to a surface of a cell culture substrate is disclosed (see patent document 6).

Of these, a structure constituted of a nanofiber having a fiber diameter of a nano level, which is formed by an electrospinning method (electrospinning) including blowing the fiber by applying a high voltage, is drawing attention as a cell culture scaffold material. Many attempts have been made to culture, on the nanofiber, functional cells and pluripotent stem cells, which are used for cell medicine and regenerative medicine, while maintaining an undifferentiated state (see non-patent document 1-non-patent document 3). However, it is difficult to impart cell adhesiveness and proliferability to such fibers derived from synthetic polymers, and they cannot be said to mimic the in vivo environment.

To improve this aspect, a nanofiber immobilizing a cell adhesive peptide containing RGD has also been studied (see non-patent document 4). In this case, cell adhesive peptide is immobilized on a synthetic polymer containing an active ester group such as N-hydroxysuccinimide (NHS) ester, for which a copolymer in consideration of hydrophilicity and hydrophobicity is used to prevent dissolution of the polymer in water. This in turn limits the amount of NHS to be introduced, the amount of an immobilizable cell adhesion substances, and consequently, the cell adhesiveness of a cell culture scaffold material.

DOCUMENT LIST

Patent Documents patent document 1: JP-A-62-502936
patent document 2: JP-A-62-122586
patent document 3: JP-A-2003-265593
patent document 4: JP-A-2005-60570
patent document 5: JP-A-2007-325543
patent document 6: U.S. Pat. No. 8,362,144

Non-Patent Document non-patent document 1: Biomaterials 26 p 5158 (2005)
non-patent document 2: Tissue Eng. 11 p 1149 (2005)
non-patent document 3: Cytotechnology 64 p 701 (2012)
non-patent document 4: Journal of Biomedical Materials Research A 100A p 794 (2012)

SUMMARY OF THE INVENTION

Problems to be Solved by the Invention

An object of the present invention is to provide a composition for producing a fiber capable of immobilizing substances effective for cell adhesion•proliferation•differentiation and the like, and retaining organic solvent resistance and liquid medium resistance, a fiber obtained by spinning the composition, and a cell culture scaffold material using the fiber.

Means of Solving the Problems

The present inventors have conducted intensive studies and found that a fiber produced by spinning a composition for producing a fiber, which contains a polymer compound having an active ester group and a hydroxy group in a side chain, a crosslinking agent, an acid compound, and a solvent can immobilize substances effective for cell adhesion•proliferation•differentiation and the like, has sufficient organic solvent resistance and further has a function as a superior cell culture scaffold material.

The present inventors have also found that, since the above-mentioned spinning of a composition for producing a fiber includes spinning a polymer compound having an active ester group and a hydroxy group in a side chain along with a crosslinking agent and an acid compound, hydroxy groups contained in the polymer compound undergo a crosslinking reaction via the crosslinking agent, and polymer compounds are crosslinked. As a result, a fiber having organic solvent resistance and liquid medium resistance is obtained.

The present inventors have found that a fiber produced by spinning the composition for producing a fiber of the present invention expresses more superior organic solvent resistance and liquid medium resistance by applying a heat treatment.

Based on these findings, the present inventors have completed the present invention.

Accordingly, the present invention provides the following.

[1] A composition for producing a fiber, comprising
- (A) a polymer compound comprising a unit structure represented by the formula (1) and a unit structure represented by the formula (2),
- (B) a crosslinking agent,
- (C) an acid compound, and
- (D) a solvent

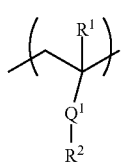

(1)

wherein
$R^1$ is a hydrogen atom or a methyl group,
$Q^1$ is an ester bond or amide bond,
$R^2$ is an alkyl group having 1-10 carbon atoms or an aromatic hydrocarbon group having 6-10 carbon atoms, wherein at least one hydrogen atom is substituted by a hydroxy group,

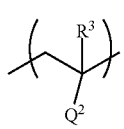

(2)

wherein
$R^3$ is a hydrogen atom or a methyl group, and
$Q^2$ is an active ester group.

[2] The composition of the above-mentioned [1], wherein the above-mentioned $Q^2$ is represented by the formula (5):

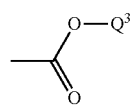

(5)

wherein $Q^3$ is an N-succinimide group, a p-nitrophenyl group or a pentafluorophenyl group.

[3] The composition of the above-mentioned [1] or [2], wherein the above-mentioned polymer compound has a weight average molecular weight of 1,000-1,000,000.

[4] The composition of any one of the above-mentioned [1]-[3], wherein the above-mentioned solvent is a polar solvent.

[5] A production method of a fiber, comprising a step of spinning the composition of any one of the above-mentioned [1]-[4].

[6] The method of the above-mentioned [5], wherein the above-mentioned spinning is electrospinning.

[7] The method of the above-mentioned [5] or [6], comprising a step of heating a spun fiber at 70-300° C.

[8] The method of any one of the above-mentioned [5]-[7], further comprising a step for immobilizing a cell adhesion substance.

[9] A fiber produced by the method of any one of the above-mentioned [5]-[8].

[10] A cell culture scaffold material comprising the fiber of the above-mentioned [9].

Effect of the Invention

According to the present invention, a composition for producing a fiber capable of immobilizing substances effective for cell adhesion•proliferation•differentiation and the like, and retaining organic solvent resistance and liquid medium resistance, a fiber obtained by spinning the composition, and a cell culture scaffold material using the fiber can be provided. Such fiber expresses a more superior function as a cell culture scaffold material by immobilizing substances effective for cell adhesion•proliferation•differentiation and the like.

DESCRIPTION OF EMBODIMENTS

1. Composition for Producing a Fiber

Figure 1:
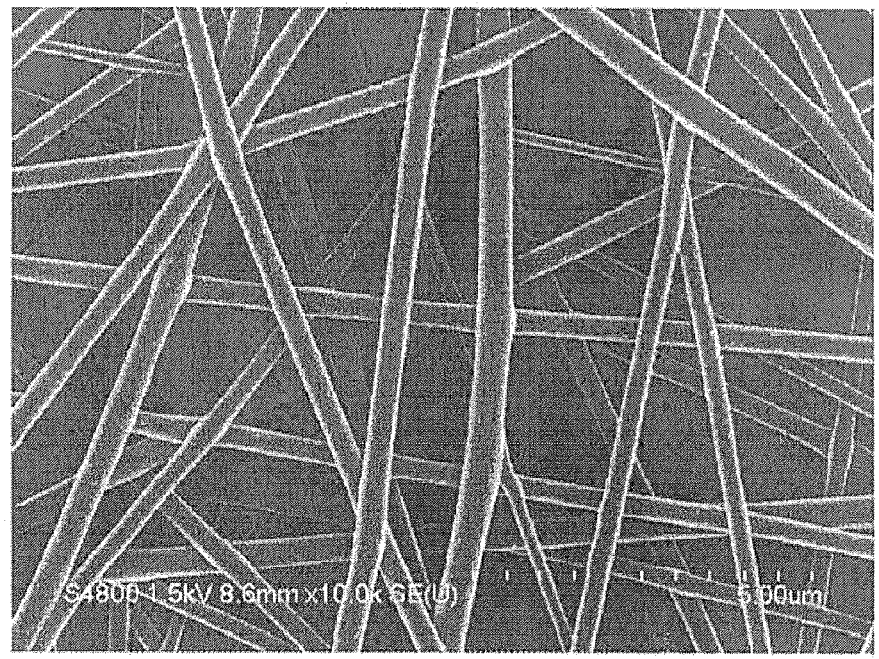
FIG. 1 is an SEM photograph of a fiber obtained from the composition of Example 1 for producing a fiber by an electrospinning method, which was taken after a heat treatment at 180° C. for 10 min.
Figure 2:
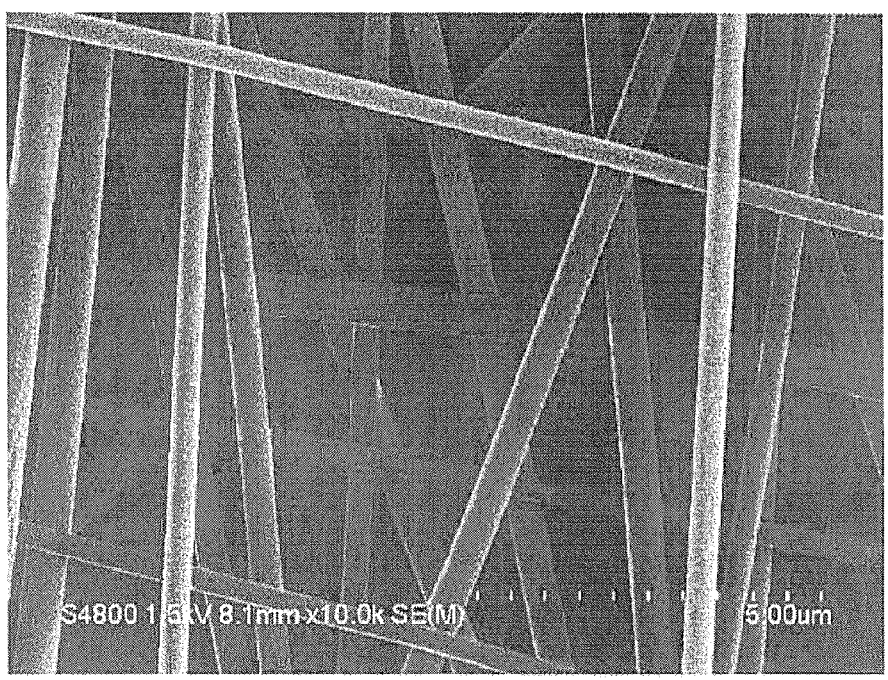
FIG. 2 is an SEM photograph of a fiber obtained from the composition of Example 4 for producing a fiber by an electrospinning method, which was taken after a heat treatment at 80° C. for 24 hr.
Figure 3:
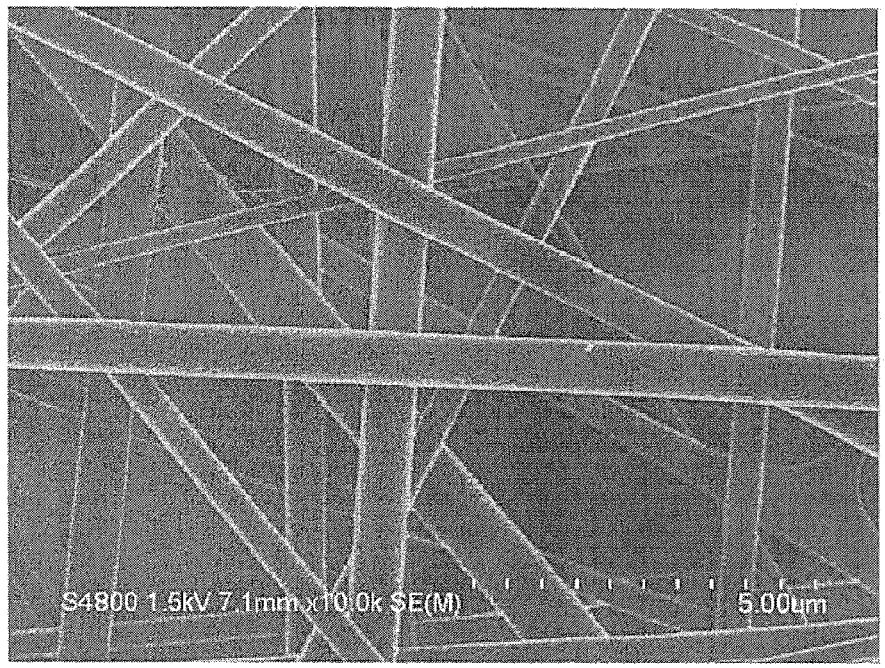
FIG. 3 is an SEM photograph of a fiber obtained from the composition of Example 4 for producing a fiber by an electrospinning method, which was taken after a heat treatment at 180° C. for 30 min.
Figure 4:
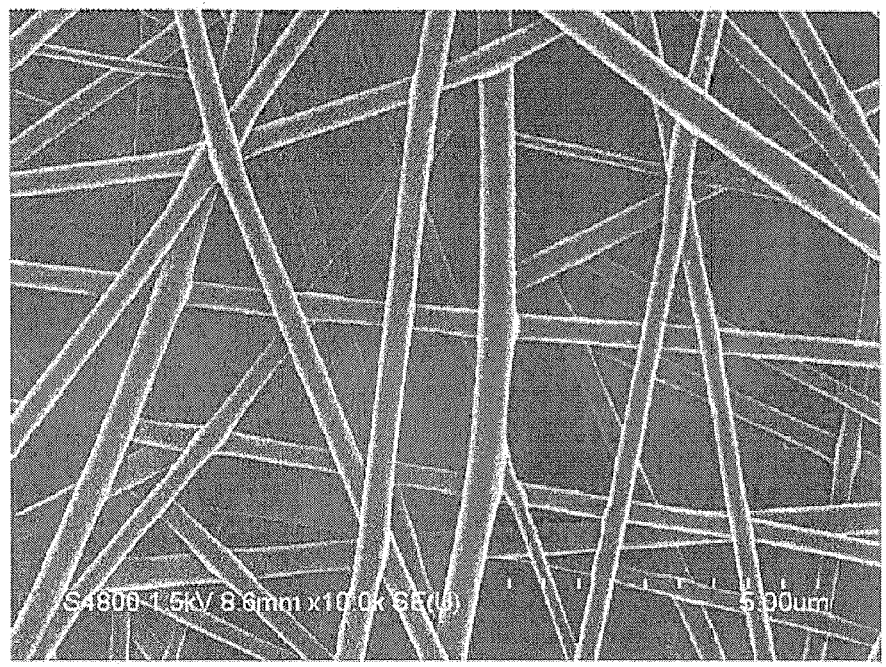
FIG. 4 is an SEM photograph of a fiber obtained from the composition of Example 1 for producing a fiber by an electrospinning method, which was taken after a heat treatment at 180° C. for 10 min and an immersion treatment in ethanol for 10 sec.
Figure 5:
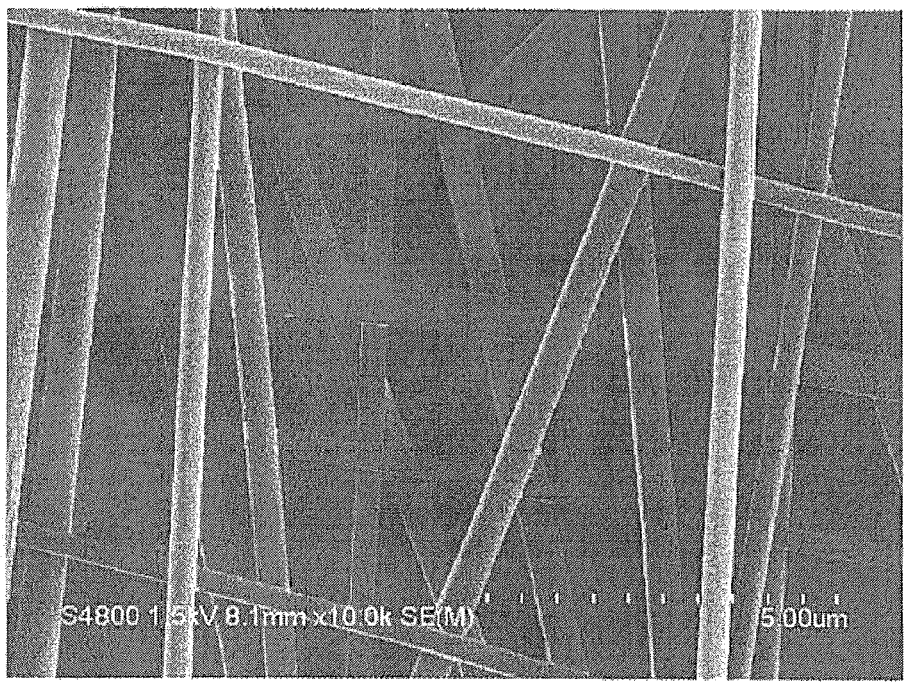
FIG. 5 is an SEM photograph of a fiber obtained from the composition of Example 4 for producing a fiber by an electrospinning method, which was taken after a heat treatment at 80° C. for 24 hr and an immersion treatment in ethanol for 10 sec.
Figure 6:
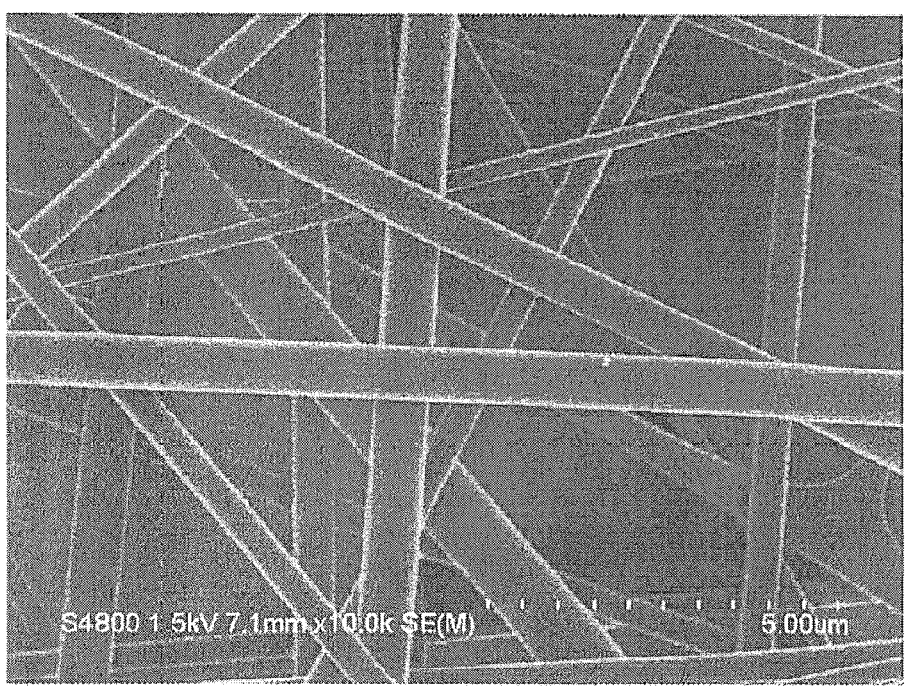
FIG. 6 is an SEM photograph of a fiber obtained from the composition of Example 4 for producing a fiber by an electrospinning method, which was taken after a heat treatment at 180° C. for 30 min and an immersion treatment in ethanol for 10 sec.
Figure 7:
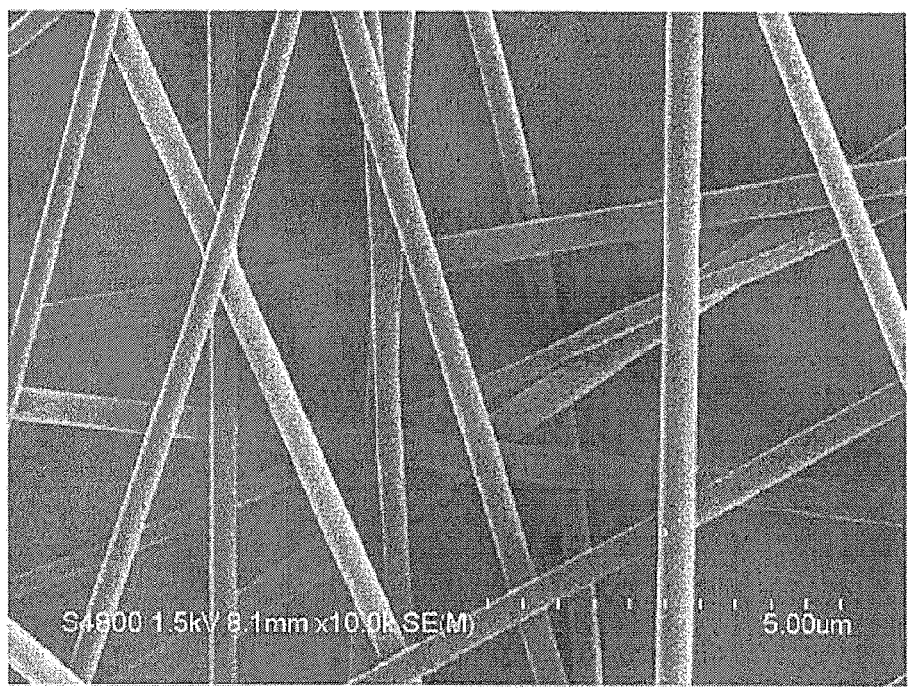
FIG. 7 is an SEM photograph of a fiber obtained from the composition of Example 5 for producing a fiber by an electrospinning method, which was taken after a heat treatment at 80° C. for 24 hr and an immersion treatment in ethanol for 10 sec.
Figure 8:
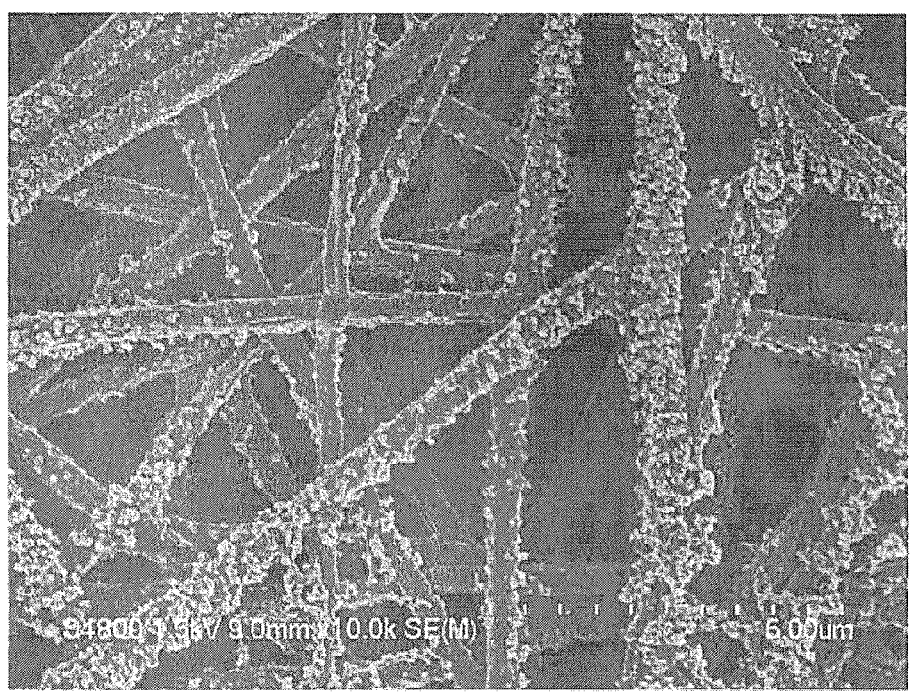
FIG. 8 is an SEM photograph of a fiber obtained from the composition of Comparative Example 2 for producing a fiber by an electrospinning method, which was taken after a heat treatment at 80° C. for 24 hr and an immersion treatment in ethanol for 10 sec.
Figure 9:
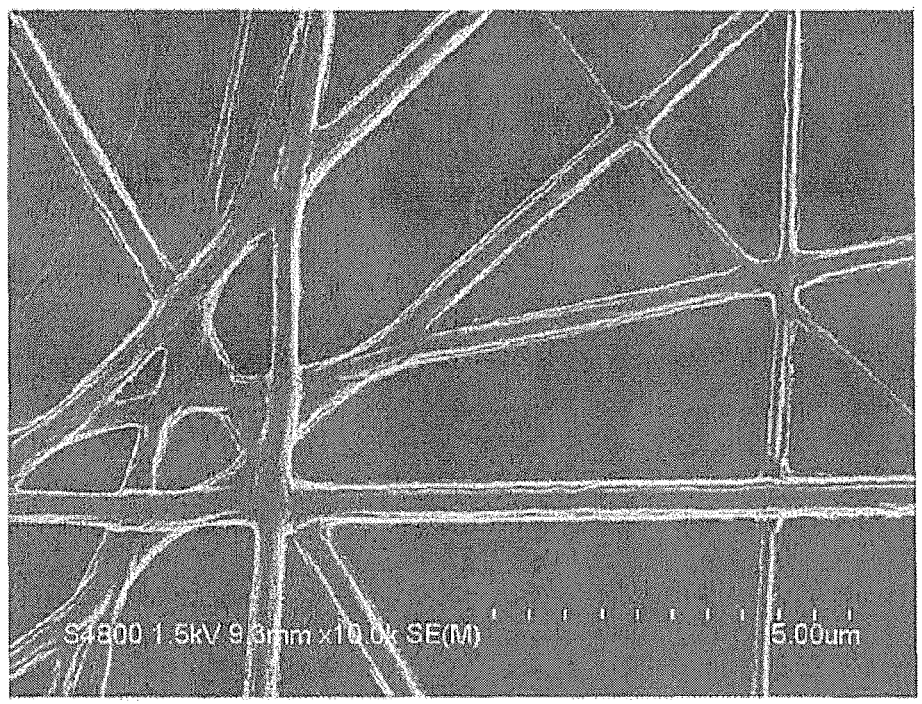
FIG. 9 is an SEM photograph of a fiber obtained from the composition of Comparative Example 4 for producing a fiber by an electrospinning method, which was taken after a heat treatment at 180° C. for 10 min and an immersion treatment in ethanol for 10 sec.
Figure 10:
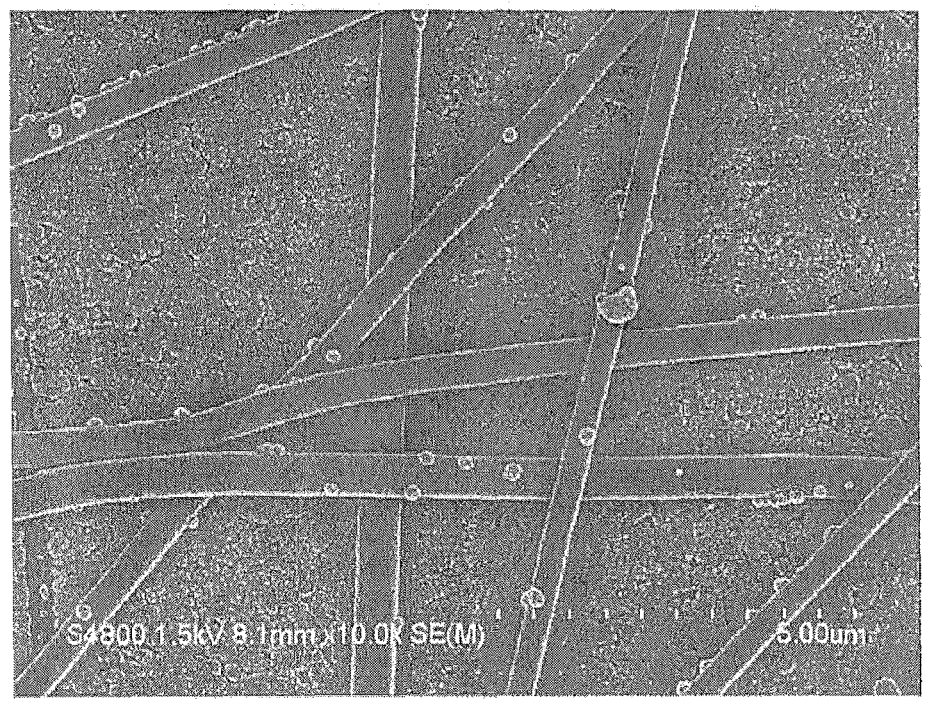
FIG. 10 is an SEM photograph of a fiber obtained from the composition of Example 4 for producing a fiber by an electrospinning method, which was taken after a heat treatment at 180° C. for 30 min and an immersion treatment in a liquid medium for 7 days.
Figure 11:
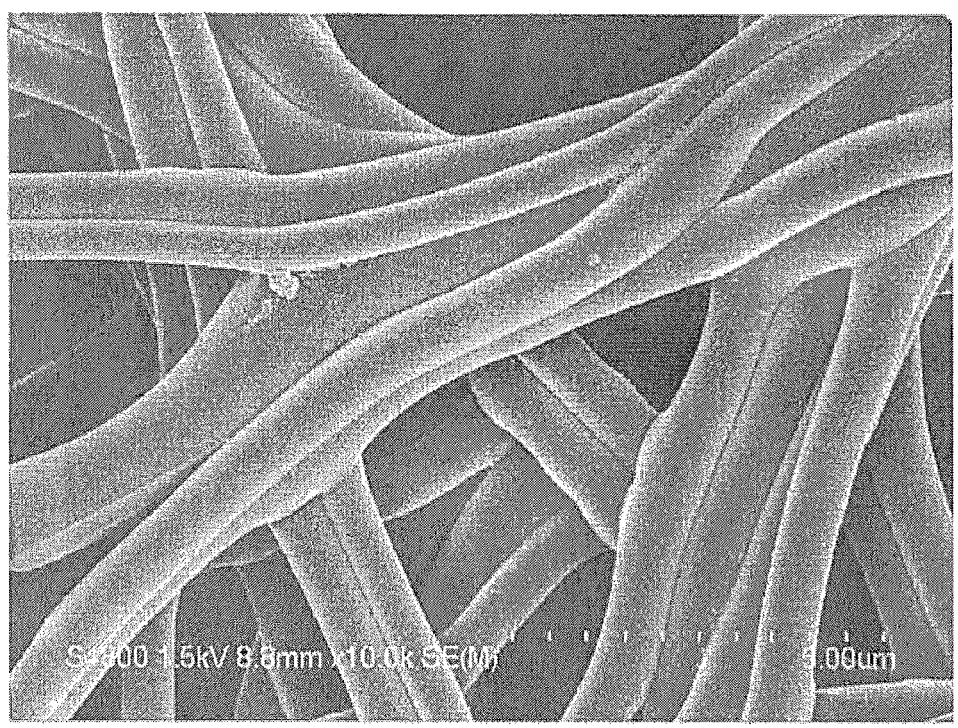
FIG. 11 is an SEM photograph of a fiber obtained from the composition of Comparative Example 1 for producing a fiber by an electrospinning method, which was taken after a heat treatment at 180° C. for 10 min and an immersion treatment in a liquid medium for 7 days.

The composition for producing a fiber of the present invention (hereinafter to be also referred to as "the composition of the present invention") is mainly characterized in that it contains (A) a polymer compound comprising a unit structure represented by the formula (1) and a unit structure represented by the formula (2), (B) a crosslinking agent, (C) an acid compound, and (D) a solvent.

[Component A]

The composition of the present invention contains, as component A, a polymer compound comprising a unit structure represented by the formula (1) and a unit structure represented by the formula (2) (hereinafter to be also referred to as "the polymer compound of component A" or simply as "component A"). Since the unit structure represented by the formula (1) contained in component A has a hydroxy group in a side chain, when component A is spun together with a crosslinking agent and an acid compound, hydroxy groups undergo a crosslinking reaction via the crosslinking agent, and polymer compounds are crosslinked to give a fiber having organic solvent resistance. In addition, since the unit structure represented by the formula (2) contained in component A has an active ester group in the side chain, it can immobilize a substance effective for cell adhesion•proliferation•differentiation and the like (cell adhesion substance) by a nucleophilic addition reaction with any amine (protein, peptide, organic amine and the like). The reaction between the active ester group of the unit structure represented by the formula (2) and any amine can be performed during preparation of the composition for producing a fiber, and can also be performed after a heat treatment after spinning the composition for producing a fiber.

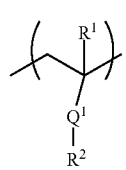

(1)

wherein
  $R^1$ is a hydrogen atom or a methyl group,
  $Q^1$ is an ester bond or an amide bond,
  $R^2$ is an alkyl group having 1-10 carbon atoms or an aromatic hydrocarbon group having 6-10 carbon atoms, wherein at least one hydrogen atom is substituted by a hydroxy group.

(2)

wherein
  $R^3$ is a hydrogen atom or a methyl group, and
  $Q^2$ is an active ester group.

The definition of each group of the formula (1) and the formula (2) is described in detail in the following.

$R^1$ is a hydrogen atom or a methyl group.

$Q^1$ is an ester bond or an amide bond, and is preferably an ester bond from the aspect of the solubility of the polymer compound of component A in a solvent.

$Q^2$ is an active ester group. In the present invention, the "active ester group" refers to an ester group wherein a carbonyl group is activated (prone to nucleophilic attack) due to an electron-attractive substituent at one of the ester groups, which is specifically an ester group represented by the formula (5).

(5)

wherein $Q^3$ is a monovalent organic group (electron-attractive group) that forms an active ester group, which is concretely exemplified by N-succinimide group, p-nitrophenyl group and pentafluorophenyl group, with preference given to N-succinimide group from the aspect of cell affinity.

$R^2$ is an alkyl group having 1-10 carbon atoms or an aromatic hydrocarbon group having 6-10 carbon atoms, wherein at least one hydrogen atom is substituted by a hydroxy group. The alkyl group having 1-10 carbon atoms may be linear or branched chain, and concrete examples thereof include methyl group, ethyl group, propyl group, isopropyl group, butyl group, isobutyl group, sec-butyl group, tert-butyl group, pentyl group, isopentyl group, neopentyl group, tert-pentyl group, 1-ethylpropyl group, hexyl group, isohexyl group, 1,1-dimethylbutyl group, 2,2-dimethylbutyl group, 3,3-dimethylbutyl group, 2-ethylbutyl group, octyl group, nonyl group, decyl group and the like. The number of the carbon atoms of the alkyl group is preferably 1-6, more preferably 1-4.

Examples of the "aromatic hydrocarbon group having 6-10 carbon atoms" of the "aromatic hydrocarbon group having 6-10 carbon atoms wherein at least one hydrogen atom is substituted by a hydroxy group" for $R^2$ include phenyl group, 1-naphthyl group, 2-naphthyl group and the like.

$R^2$ is preferably an alkyl group having 1-10 (more preferably 1-6, particularly preferably 1-4) carbon atoms wherein at least one hydrogen atom is substituted by a hydroxy group, or a phenyl group wherein at least one hydrogen atom is substituted by a hydroxy group from the aspects of the efficiency of the crosslinking reaction during fiber production and cell affinity of the produced fiber.

$R^3$ is a hydrogen atom or a methyl group.

In a preferable unit structure represented by the formula (1), $R^1$ is a hydrogen atom or a methyl group, $Q^1$ is an ester bond, $R^2$ is an alkyl group having 1-10 (more preferably 1-6, particularly preferably 1-4) carbon atoms, wherein at least one hydrogen atom is substituted by a hydroxy group, or a phenyl group wherein at least one hydrogen atom is substituted by a hydroxy group.

The unit structure represented by the formula (1) is preferably a unit structure represented by the formula (3).

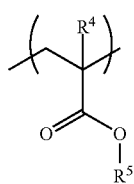

(3)

wherein $R^4$ is as defined for the above-mentioned $R^1$, $R^5$ is as defined for the above-mentioned $R^2$.

The unit structure represented by the formula (2) is preferably a unit structure represented by the formula (4).

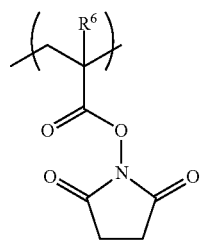

(4)

wherein $R^6$ is a hydrogen atom or a methyl group.

In the polymer compound of component A, the composition ratio of the unit structure represented by the formula (1) and the composition ratio of the unit structure represented by the formula (2) are preferably (unit structure represented by the formula (1))/(unit structure represented by the formula (2))=(35-95 mol %)/(5-65 mol %), from the aspects of easiness of synthesis, solubility in solvent, easiness of fiber formation, and effect of immobilization of any amine. The composition ratios of these unit structures can be measured by $^{13}$C-NMR.

While the polymer compound of component A may contain a unit structure other than the unit structure represented by the formula (1) and the unit structure represented by the formula (2) as long as the object of the present invention is not impaired, from the aspect of polymerizability of the polymer compound of component A, the ratio (mol %) of the unit structure represented by the formula (1) is preferably 35-95 mol %, and the ratio (mol %) of the unit structure represented by the formula (2) is preferably 5-65 mol %, each relative to the total unit structure in the polymer compound of component A. In addition, the total (mol %) of the ratio of the unit structure represented by the formula (1) and the ratio of the unit structure represented by the formula (2), each relative to the total unit structure in the polymer compound of component A, preferably exceeds 90 mol %, more preferably not less than 95 mol %, particularly preferably 100 mol %, from the aspect of polymerizability of the polymer compound of component A. The ratio of each unit structure to the total unit structure in the polymer compound of component A can be calculated from the composition ratio of each unit structure measured by $^{13}$C-NMR.

The weight average molecular weight of component A is preferably 1,000-1,000,000, more preferably 5,000-500,000, particularly preferably 10,000-300,000, from the aspects of the organic solvent resistance of the fiber using the above-mentioned composition. In the present invention, the "weight average molecular weight" refers to a molecular weight based on polystyrene, which is measured by gel permeation chromatography (GPC).

Component A can be produced by a method known per se or a method analogous thereto. For example, it can be produced by polymerizing monomers corresponding to the unit structure represented by the formula (1) and monomers corresponding to the unit structure represented by the formula (2) in a suitable solvent (e.g., acetonitrile etc.) by using a suitable polymerization initiator (e.g., dimethyl 2,2'-azobis(isobutyrate) etc.) and the like, but the method is not limited thereto. A commercially available product can also be used.

Examples of the monomer corresponding to the unit structure represented by the formula (1) include 2-hydroxyethyl (meth)acrylate (e.g., compound of CAS number: 868-77-9), 2-hydroxypropyl (meth)acrylate (e.g., compound of CAS number: 923-26-2), 4-hydroxybutyl (meth)acrylate (e.g., compound of CAS number: 2478-10-6), N-hydroxymethyl (meth)acrylamide (e.g., compound of CAS number: 923-02-4), N-(2-hydroxyethyl) (meth)acrylamide (e.g., compound of CAS number: 5238-56-2), N-(2-hydroxypropyl) (meth)acrylamide (e.g., compound of CAS number: 26099-09-2), p-hydroxy (meth)acrylic anilide (e.g., compound of CAS number: 19243-95-9) and the like. Preferred is 2-hydroxyethyl (meth)acrylate or 2-hydroxypropyl (meth)acrylate, and most preferred is 2-hydroxypropyl (meth)acrylate.

In the present invention, the "(meth)acrylate compound" refers to both an acrylate compound and a methacrylate compound. For example, (meth)acrylic acid refers to both acrylic acid and methacrylic acid.

Preferable examples of the monomer corresponding to the unit structure represented by the formula (2) include p-nitrophenyl (meth)acrylate (e.g., compound of CAS number: 16522-41-1), pentafluorophenyl (meth)acrylate (e.g., compound of CAS number: 13642-97-2), N-acrylicoxysuccinimide (compound of CAS number: 38862-24-7), N-succinimidyl methacrylate (compound of CAS number: 38862-25-8), and N-succinimidyl methacrylate is most preferable.

The content ratio of component A in the composition of the present invention is preferably 5-50 wt %, more preferably 10-40 wt %, from the aspects of the production of a fiber having an appropriate thickness.

[Component B]

The composition of the present invention contains, as component B, a crosslinking agent (hereinafter to be also referred to as "the crosslinking agent of component B" or simply as "component B"). Component B when used in combination with the below-mentioned component C crosslinks hydroxy groups of component A via component B itself to impart organic solvent resistance to the fiber.

Examples of the crosslinking agent of component B include aminoplast crosslinking agents such as 1,3,4,6-tetrakis(methoxymethyl)glycoluril, 1,3,4,6-tetrakis(butoxymethyl)glycoluril and the like; phenoplast crosslinking agents such as 2,2-bis(4-hydroxy-3,5-dihydroxymethylphenyl)propane and the like; isocyanate crosslinking agents such as hexamethylene diisocyanate and the like; vinylether crosslinking agents such as 1,4-bis(vinyloxy)butane and the like; and the like.

Component B is preferably an aminoplast crosslinking agent, which is preferably 1,3,4,6-tetrakis(hydroxymethyl) glycoluril (CAS number: 5395-50-6), 1,3,4,6-tetrakis (methoxymethyl)glycoluril (CAS number: 17464-88-9), 1,3,4,6-tetrakis(ethoxymethyl)glycoluril (CAS number: 65952-06-9), 1,3,4,6-tetrakis(1-methylethoxy)glycoluril (CAS number: 508220-69-7), 1,3,4,6-tetrakis(1,1-dimethylethoxy)glycoluril (CAS number: 547744-08-1) or 1,3,4,6-tetrakis(butoxymethyl)glycoluril (CAS number: 15968-37-3), more preferably 1,3,4,6-tetrakis(methoxymethyl) glycoluril.

Component B may be used alone, or two or more kinds thereof may be used in combination.

The crosslinking agent of component B can be produced by a method known per se or a method analogous thereto. In addition, a commercially available product may also be used.

The content ratio of component B in the composition of the present invention is preferably 0.1-5 wt %, more preferably 0.2-3 wt %, from the aspects of the reaction efficiency with component A.

The weight ratio of component A and component B (weight of component A/weight of component B) contained in the composition of the present invention is preferably 5-65, more preferably 5-25, from the aspects of the reaction efficiency during fiber production.

[Component C]

The composition of the present invention contains, as component C, an acid compound (hereinafter to be also referred to as "the acid compound of component C" or simply as "component C"). The acid compound may be in the produce of a salt; that is, the term "acid compound" in the present invention is a concept encompassing even a salt. Component C used in combination with component B can promote a crosslinking reaction of hydroxy groups of component A when the crosslinking reaction occurs via component B.

Examples of the acid compound of component C include organic acid compounds such as sulfonic acid compound, carboxylic acid compound and the like; inorganic acid compounds such as hydrochloric acid, phosphoric acid, sulfuric acid, nitric acid, hydrobromic acid and the like, and the like.

Component C is preferably an organic acid compound, more preferably a sulfonic acid compound. Examples of the sulfonic acid compound include p-toluenesulfonic acid, pyridinium p-toluenesulfonate, trifluoromethanesulfonic acid and the like, with preference given to pyridinium p-toluenesulfonate.

Component C may be used alone, or two or more kinds thereof may be used in combination.

The acid compound of component C can be produced by a method known per se or a method analogous thereto. In addition, a commercially available product may also be used.

The content ratio of component C in the composition of the present invention is preferably 0.01-1.0 wt %, more preferably 0.05-0.5 wt %, particularly preferably 0.07-0.4 wt %, from the aspects of the crosslinking reaction rate and crosslinking reaction efficiency.

The weight ratio of component A and component C (weight of component A/weight of component C) contained in the composition of the present invention is preferably 20-120, more preferably 80-115, from the aspects of the crosslinking reaction rate and crosslinking reaction efficiency.

[Component D]

The composition of the present invention contains, as component D, a solvent (hereinafter to be also referred to as "the solvent of component D" or simply as "component D").

The solvent of component D is not particularly limited as long as it can uniformly dissolve or disperse at least the above-mentioned components A-C, and does not react with each is component. From the aspects of solubility of components A-C, a polar solvent is preferable.

Examples of the polar solvent include water, methanol, ethanol, 2-propanol, propylene glycol monomethyl ether, acetone, dimethylformamide, dimethylacetamide, N-methylpyrrolidone and the like. Preferred for easy spinning of the composition is a mixed solvent of acetone and dimethylacetamide, and a preferable mixing ratio (wt %) thereof is acetone/dimethylacetamide=(90 wt %-60 wt %)/(10 wt %-40 wt %).

Component D may be used alone, or two or more kinds thereof may be used in combination.

The composition of the present invention may contain, as necessary besides components A-D, an additive generally used for a composition for producing a fiber as long as the object of the present invention is not markedly impaired. Examples of the additive include surfactant, rheology adjusting agent, chemical agent, fine particles and the like.

The composition of the present invention can be prepared by mixing the above-mentioned components A-D, or components A-D and the above-mentioned additive. The mixing method is not particularly limited, and a method known per se or a method analogous thereto can be used for mixing.

The composition of the present invention can be used for fiber production. The kind of the fiber produced using the composition of the present invention is not particularly limited. For example, when used as a biocompatible material (e.g., cell culture scaffold material etc.) and the like, nanofiber, microfiber and the like are preferable, and nanofiber is more preferable. In the present invention, "nanofiber" refers to a fiber having a diameter of a nano meter order (e.g., 1-1000 nm), and the "microfiber" refers to a fiber having a diameter of a micro meter order (e.g., 1-1000 μm).

While the diameter of the fiber formed using the composition of the present invention can be appropriately adjusted according to the use of fiber and the like, it is preferably 1-1000 nm, more preferably 10-1000 nm, from the aspects of the concentration of the composition of the present invention, and easiness of spinning. In the present invention, the diameter of a fiber is measured by a scanning electron microscope (SEM).

2. Production Method of Fiber, Fiber Produced by the Production Method

The production method of the fiber of the present invention (hereinafter to be also referred to as "the method of the present invention") is mainly characterized in that it contains a step of spinning the composition of the present invention.

The spinning method of the composition of the present invention is not particularly limited as long as it can form a fiber. For example, melt blow method, composite melt spinning method, electrospinning method and the like can be mentioned, and electrospinning method is preferable from the aspect of the fiber forming ability.

Electrospinning method is a known spinning method, and can be performed using a known electrospinning apparatus. Various conditions such as the speed of discharging the composition of the present invention from the tip of a nozzle (e.g., needle etc.) (discharge speed); application voltage; the distance between the tip of a nozzle discharging the composition of the present invention and a substrate for receiving same (discharge distance) and the like can be appropriately determined according to the diameter of the fiber to be produced and the like. The discharge speed is generally 0.1-100 µl/min, preferably 0.5-50 µl/min, more preferably 1-20 µl/min. The application voltage is generally 0.5-80 kV, preferably 1-60 kV, more preferably 3-40 kV. The discharge distance is generally 1-60 cm, preferably 2-40 cm, more preferably 3-30 cm.

The method of the present invention preferably further includes a step of spinning the composition of the present invention, and heating the spun fiber at a particular temperature. By heating a spun fiber at a particular temperature, more superior resistance to organic solvents can be expressed.

The temperature for heating a spun fiber is generally 70-300° C. From the aspects of the reactivity of the crosslinking agent of component B, and the heat resistance of the polymer compound of component A, it is preferably 80-250° C., more preferably 90-200° C. When the temperature is less than 70° C., the crosslinking reaction of components A becomes insufficient, and the produced fiber tends to show lower resistance to organic solvents. When it exceeds 300° C., the polymer compound of component A itself undergoes decomposition or dissolution due to the heat and the like, and a fiber cannot be formed.

The heating method of the spun fiber is not particularly limited as long as heating at the above-mentioned heating temperature is possible, and a method known per se or a method analogous thereto can be appropriately used for heating. Specific examples of the heating method include a method using a hot plate, oven and the like under atmosphere, and the like.

While the heating time of the spun fiber can be appropriately determined according to the heating temperature and the like, it is preferably 1 min-48 hr, more preferably 5 min-36 hr, particularly preferably 10 min-24 hr from the aspects of crosslinking reaction rate, and production efficiency.

While the kind of the fiber to be produced by the method of the present invention (hereinafter to be also referred to as "the fiber of the present invention") is not particularly limited, for example, nanofiber, microfiber and the like are preferable, and nanofiber is more preferable, when used for a biocompatible material (e.g., cell culture scaffold material etc.) and the like.

While the diameter of the fiber of the present invention can be appropriately adjusted according to the use of fiber and the like, for example, when the fiber is used as a material of cell culture scaffold, it is preferably 1-1000 nm, more preferably 10-1000 nm, from the aspects of the efficiency of cell culture.

While the use of the fiber of the present invention is not particularly limited, the fiber is suitable as a material of cell culture scaffold since it has superior resistance to organic solvents and has sufficient function as cell culture scaffold.

A supporting substance (cell adhesion substance) effective for the cell adhesion•proliferation•differentiation and the like can be immobilized on the aforementioned fiber by a reaction between an active ester group present in the fiber of the present invention and a cell adhesion substance.

An active ester group reacts with a free primary amino group under neutral conditions. The basicity of primary amine is stronger in alkylamine than aromatic amine, and alkylamine is more suitable for reaction with active ester.

When protein and peptide are added to a fiber by a covalent bond via the amino groups thereof, a reaction in a water system is essential, and the reaction proceeds in a short time when the reaction solution has a pH in the neutral to weak alkaline region, or the reaction temperature is ice-cooling to about 37° C. In the case of primary amine having low water-solubility, it is preferable to perform reaction by dissolving same in an organic solvent such as ethanol, dimethyl sulfoxide and the like.

Preferable reaction conditions are 0° C.-37° C. for 1-48 hr, further preferably 0° C.-37° C. for 1-24 hr.

Examples of the substance that can be immobilized on the fiber of the present invention (cell adhesion substance) include protein, physiologically active substance and compound and the like. Examples of the aforementioned protein include disease markers such as carcinoembryonic antigen, squamous cell carcinoma related antigen, cytokeratin 19 fragment, sialylated carbohydrate antigen KL-6, natriuretic peptide, troponin, myoglobulin and the like, cell growth factors such as interleukin-1 (IL-1), interleukin-2 (IL-2), interleukin-3 (IL-3), interleukin-4 (IL-4), interleukin-5 (IL-5), interleukin-6 (IL-6), interleukin-7 (IL-7), interleukin-8 (IL-8), interleukin-9 (IL-9), interleukin-10 (IL-10), interleukin-11 (IL-11), interleukin-12 (IL-12), interleukin-13 (IL-13), interleukin-14 (IL-14), interleukin-15 (IL-15), interleukin-18 (IL-18), interleukin-21 (IL-21), interferon-α (IFN-α), interferon-β (IFN-β), interferon-γ (IFN-γ), granulocyte colony stimulating factor (G-CSF), monocyte colony stimulating factor (M-CSF), granulocyte-macrophage colony stimulating factor (GM-CSF), stem cell factor (SCF), flk2/flt3 ligand (FL), leukemia cell inhibitory factor (LIF), oncostatin M (OM), erythropoietin (EPO), thrombopoietin (TPO), transforming growth factor-α (TGF-α), transforming growth factor-β (TGF-β), macrophage inflammation protein-la (MIP-1α), epithelial cell growth factor (EGF), fibroblast growth factor-1, 2, 3, 4, 5, 6, 7, 8, or 9 (FGF-1, 2, 3, 4, 5, 6, 7, 8, 9), nerve cell growth factor (NGF), hepatocyte growth factor (HGF), leukemia inhibitory factor (LIF), proteasenexin I, proteasenexin II, platelet-derived growth factor (PDGF), cholinergic differentiation factor (CDF), chemokine, Notch ligand (Delta 1 and the like), Wnt protein, angiopoietin-like protein 2, 3, 5 or 7 (Angpt 2, 3, 5, 7), insulin-like growth factor (IGF), insulin-like growth factor binding protein-1 (IGFBP), Pleiotrophin, insulin, growth hormone and the like, and cell adhesion factors such as collagen I to XIX, fibronectin, vitronectin, laminin-1 to 12, laminin 511, laminin 521, nitrogen, tenascin, thrombospondin, von Willebrand (von Willebrand) factor, osteopontin, fibrinogen, various elastin, various proteoglycan, various cadherin, desmocollin, desmoglein, various integrin, E-selectin, P-selectin, L-selectin, immunoglobulin superfamily, matrigel, poly-D-lysine, poly-L-lysine and the like, various antibodies such as IgG, IgM, IgA, IgD, IgE and the like and the like.

Examples of the aforementioned physiologically active substance include saccharides such as D-glucosamine, D-galactosamine, neuraminic acid, hyaluronic acid, chondroitin sulfate, heparan sulfuric acid, heparin and the like, serotonin noradrenaline, adrenaline, 3-(3,4-dichlorophenyl)-1,1-dimethylurea (DCMU), atrazine, linuron and simazine and the like.

Examples of the aforementioned compound include peptides such as angiotensin I to IV, bradykinin, fibrinopeptide, natriuretic peptide, urodilatin, guanylin, endothelin 1 to 3, salusin, urotensin, oxytocin, neurophysin, vasopressin, adrenocorticotropic hormone, melanocyte-stimulating hormone, endorphin, lipotropin, urocrtin 1 to 3, luteinizing hormone releasing homone, growth hormone releasing homone, somatostatin, cortistatin, prolactin releasing peptide, metastin, tachykinin, substance P, neurokinin, endokinin, neurotension, neuromedin, xenin, ghrelin, obestatin, melanin-concentrating hormone, orexin, neuropeptide, dynorphin, neoendorphin, endomorphine, nociceptin, pyroglutamylated RF amide peptide, galanin, gastrin, cholecystokinin, secretin, relaxin, glucagon, glicentin, adrenomedullin, amylin, calcitonin, parathyroid hormone, defensin, thymosin, YIGSR peptide and the like; amino acids such as alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, cystine, hydroxyproline, hydroxylysine, dihydroxyphenylalanine, thyroxine, phosphoserine, desmosine, β-alanine, sarcosine, ornithine, creatine, γ-amino butyric acid, theanine, kainic acid, domoic acid, ibotenic acid and the like; primary amines such as 2-dimethylaminoethylamine (compound of CAS number: 108-00-9), N-(2-hydroxyethyl)ethylenediamine (compound of CAS number: 111-41-1), N-(2-aminoethyl)piperazine (compound of CAS number: 140-31-8), 4-(2-aminoethyl)morpholine (compound of CAS number: 2038-03-1), 1-(2-aminoethyl)-2-imidazolidinone (compound of CAS number: 6281-42-1), tryptamine (compound of CAS number: 61-54-1), histamine dihydrochloride (compound of CAS number: 56-92-8), tyramine (compound of CAS number: 51-67-2), dopamine (compound of CAS number: 51-61-6) and the like; primary diamines such as ethylenediamine dihydrochloride (compound of CAS number: 333-18-6), 1,6-diaminohexane (compound of CAS number: 124-09-4), N,N'-bis(aminopropyl)piperazine (compound of CAS number: 7209-38-3) and the like.

Of these, a particularly preferable cell adhesion substance is laminin 511, laminin 521 or YIGSR peptide.

3. Cell Culture Scaffold Material

The cell culture scaffold material of the present invention is mainly characterized in that it contains the fiber of the present invention. In the present invention, the "cell culture scaffold material" refers to a material permitting cell culture without exerting an adverse influence on the cell.

Examples of the cell culture scaffold material of the present invention include a cell culture substrate obtained by spraying the fiber of the present invention on glass, metal or plastic such as polystyrene (e.g., 6 well flat-bottom microplate etc.), a culture bag introduced with the fiber of the present invention and the like. Furthermore, a substance for immobilization via an active ester group (cell adhesion substance) can promote cell proliferation, induce differentiation of cell and the like.

The cell to be cultured using the cell culture scaffold material of the present invention is not particularly limited and, for example, fibroblast, bone marrow cell, B lymphocyte, T lymphocyte, neutrophil, red blood cell, platelet, macrophage, monocyte, osteocyte, bone marrow cell, pericyte, dendritic cell, keratinocyte, adipocyte, mesenchyme cell, epithelial cell, epidermal cell, endothelial cell, vascular endothelial cell, hepatocyte, chondrocyte, cumulus cell, nerve system cell, glial cell, neuron, oligodendrocyte, microglia, astrocyte, cardiocyte, esophagus cell, myocytes (e.g., smooth muscle cell or skeleton muscle cell), pancreas beta cell, melanocyte, hematopoietic progenitor cell, mononuclear cell, embryonic stem cells (ES CELL), embryonic tumor cell, embryonic germ cell, induced pluripotent stem cell (iPS cell), neural stem cell, hematopoietic stem cell, mesenchymal stem cell, liver stem cell, pancreas stem cell, muscle stem cell, reproductive stem cell, intestinal stem cell, cancer stem cell, hair follicle stem cell, and various cell line (e.g., HCT116, Huh7, HEK293 (human embryonic kidney cell), HeLa (human head and neck cancer cell line), HepG2 (human liver cancer cell line), UT7/TPO (human leukemia cell line), CHO (Chinese hamster ovary cell line), MDCK, MDBK, BHK, C-33A, HT-29, AE-1, 3D9, Ns0/1, Jurkat, NIH3T3, PC12, S2, Sf9, Sf21, High Five, Vero) and the like can be mentioned.

The cell culture scaffold material of the present invention can be produced using the fiber of the present invention as one of the starting materials and according to a method known per se or a method analogous thereto.

EXAMPLES

While specific examples of the present invention are explained below, the present invention is not limited in any way by the examples.

[Measurement of Weight Average Molecular Weight of Polymer Compounds 1-6]

The weight average molecular weight of the following polymer compounds 1-6 is measured by gel permeation chromatography (GPC). The apparatus used for the measurement and measurement conditions are as follows.
  apparatus: TOSOH HLC-8320GPC system
  column: Shodex (registered trade mark) KF-803L, KF-802 and KF-801
  column temperature: 40° C.
  eluent: DMF
  flow rate: 0.6 ml/min
  detector: RI
  standard sample: polystyrene

[$^{13}$C-NMR Measurement of Polymer Compound of Component A]

The composition ratio of the unit structure of the following polymer compound of component A is measured by $^{13}$C-NMR. The apparatus and conditions used for the measurement and analysis were as follows.
  apparatus: JEOL Ltd. JNM-ECA500, Delta V5.0
  measurement nucleus: $^{13}$C gated decoupling
  cumulated number: 18000
  measurement temperature: room temperature
  detection peak: 69-71 ppm (derived from HPMA),
  25-27 ppm (derived from NSuMA)
  measurement solvent: deuterated dimethyl sulfoxide (DMSO-$d_6$), 750 uL
  sample amount: 0.1 g
  mitigation reagent: chrome(III) acetylacetonate, 4 mg Synthetic Example (Synthesis of Polymer Compounds 1-6)

Synthetic Example 1: Polymer Compound 1

2-Hydroxypropyl methacrylate (HPMA; manufactured by Tokyo Chemical Industry Co., Ltd.) (10.5 g), N-succinimidyl methacrylate (NSuMA; manufactured by Tokyo Chemical Industry Co., Ltd.) (1.5 g), and dimethyl 2,2'-azobis(2-methylpropionate) (MAIB; manufactured by Wako Pure Chemical Industries, Ltd.) (0.01 g) were dissolved in acetonitrile (28.3 g), and added dropwise to acetonitrile (20.2 g) heated under reflux under a nitrogen atmosphere. After the completion of the dropwise addition, the mixture was reacted for 17 hr with heating under reflux. Diethyl ether was added to this reaction mixture to allow for precipitation of the polymer. The polymer was collected by filtration, and dried under reduced pressure to give polymer compound 1 (7.71 g). The weight average molecular weight of the polymer compound 1 was 217,000 based on polystyrene. The composition ratio measured by $^{13}$C-NMR was HPMA/NSuMA-91 mol %/9 mol %.

Synthetic Example 2: Polymer Compound 2

2-Hydroxypropyl methacrylate (HPMA; manufactured by Tokyo Chemical Industry Co., Ltd.) (10.6 g), N-succinimidyl methacrylate (NSuMA; manufactured by Tokyo Chemical Industry Co., Ltd.) (1.5 g), and dimethyl 2,2'-azobis(2-methylpropionate) (MAIB; manufactured by Wako Pure Chemical Industries, Ltd.) (0.72 g) were dissolved in acetonitrile (30.0 g), and added dropwise to acetonitrile (21.4 g) heated under reflux under a nitrogen atmosphere. After the completion of the dropwise addition, the mixture was reacted for 17 hr with heating under reflux. Diethyl ether was added to this reaction mixture to allow for precipitation of the polymer. The polymer was collected by filtration, and dried under reduced pressure to give polymer compound 2 (12.0 g). The weight average molecular weight of the polymer compound 2 was 13,000 based on polystyrene. The composition ratio measured by $^{13}$C-NMR was HPMA/NSuMA-92 mol %/8 mol %.

Synthetic Example 3: Polymer Compound 3

2-Hydroxypropyl methacrylate (HPMA; manufactured by Tokyo Chemical Industry Co., Ltd.) (33.0 g), N-succinimidyl methacrylate (NSuMA; manufactured by Tokyo Chemical Industry Co., Ltd.) (18.0 g), and dimethyl 2,2'-azobis(2-methylpropionate) (MAIB; manufactured by Wako Pure Chemical Industries, Ltd.) (0.05 g) were dissolved in acetonitrile (119.2 g), and added dropwise to acetonitrile (85.2 g) heated under reflux under a nitrogen atmosphere. After the completion of the dropwise addition, the mixture was reacted for 17 hr with heating under reflux. Thereafter, the reaction mixture was concentrated to the amount of about 100 ml, diethyl ether was added to allow for precipitation of the polymer. The polymer was collected by filtration, and dried under reduced pressure to give polymer compound 3 (36.0 g). The weight average molecular weight of the polymer compound 3 was 182,000 based on polystyrene. The composition ratio measured by $^{13}$C-NMR was HPMA/NSuMA=62 mol %/38 mol %.

Synthetic Example 4: Polymer Compound 4

2-Hydroxypropyl methacrylate (HPMA; manufactured by Tokyo Chemical Industry Co., Ltd.) (8.3 g), N-succinimidyl methacrylate (NSuMA; manufactured by Tokyo Chemical Industry Co., Ltd.) (7.0 g), and dimethyl 2,2'-azobis(2-methylpropionate) (MAIB; manufactured by Wako Pure Chemical Industries, Ltd.) (0.01 g) were dissolved in acetonitrile (35.7 g), and added dropwise to acetonitrile (25.5 g) heated under reflux under a nitrogen atmosphere. After the completion of the dropwise addition, the mixture was reacted for 17 hr with heating under reflux. Diethyl ether was added to this reaction mixture to allow for precipitation of the polymer. The polymer was collected by filtration, and dried under reduced pressure to give polymer compound 4 (11.0 g). The weight average molecular weight of the polymer compound 4 was 265,000 based on polystyrene. The composition ratio measured by $^{13}$C-NMR was HPMA/NSuMA=50 mol %/50 mol %.

Synthetic Example 5: Polymer Compound 5

2-Hydroxypropyl methacrylate (HPMA; manufactured by Tokyo Chemical Industry Co., Ltd.) (5.5 g), N-succinimidyl methacrylate (NSuMA; manufactured by Tokyo Chemical Industry Co., Ltd.) (7.0 g), and dimethyl 2,2'-azobis(2-methylpropionate) (MAIB; manufactured by Wako Pure Chemical Industries, Ltd.) (0.01 g) were dissolved in acetonitrile (29.2 g), and added dropwise to acetonitrile (20.9 g) heated under reflux under a nitrogen atmosphere. After the completion of the dropwise addition, the mixture was reacted for 17 hr with heating under reflux. Diethyl ether was added to this reaction mixture to allow for precipitation of the polymer. The polymer was collected by filtration, and dried under reduced pressure to give polymer compound 5 (8.9 g). The weight average molecular weight of the polymer compound 5 was 113,000 based on polystyrene. The composition ratio measured by $^{13}$C-NMR was HPMA/NSuMA=37 mol %/63 mol %.

Synthetic Example 6: Polymer Compound 6

Methyl methacrylate (MMA; manufactured by Tokyo Chemical Industry Co., Ltd.) (10.0 g) and dimethyl 2,2'-azobis(2-methylpropionate) (MAIB; manufactured by Wako Pure Chemical Industries, Ltd.) (0.01 g) were dissolved in acetonitrile (23.4 g), and added dropwise to acetonitrile (16.7 g) heated under reflux under a nitrogen atmosphere. After the completion of the dropwise addition, the mixture was reacted for 17 hr with heating under reflux. Diethyl ether was added to this reaction mixture to allow for precipitation of the polymer. The polymer was collected by filtration, and dried under reduced pressure to give polymer compound 6 (5.3 g). The weight average molecular weight of the polymer compound 6 was 230,000 based on polystyrene.

In the aforementioned polymer compounds 1-5, when a uniform polymer solution was obtained after the polymerization reaction, "good" is indicated, and when a uniform polymer solution was not obtained, "failure" is indicated in Table 1.

TABLE 1

| polymer compound | charged ratio (mol %) of each monomer | | charged ratio (mol %) to total monomer | composition ratio (mol %) of each monomer | | polymerizability (weight average molecular weight) |
|---|---|---|---|---|---|---|
| | HPMA | NSuMA | MAIB | HPMA | NSuMA | |
| 1 | 90 | 10 | 0.06 | 91 | 9 | good (217,000) |
| 2 | 90 | 10 | 3.8 | 92 | 8 | good (13,000) |
| 3 | 70 | 30 | 0.07 | 62 | 38 | good (182,000) |
| 4 | 60 | 40 | 0.07 | 50 | 50 | good (265,000) |

TABLE 1-continued

| polymer compound | charged ratio (mol %) of each monomer | | charged ratio (mol %) to total monomer | composition ratio (mol %) of each monomer | | polymerizability (weight average molecular weight) |
|---|---|---|---|---|---|---|
| | HPMA | NSuMA | MAIB | HPMA | NSuMA | |
| 5 | 50 | 50 | 0.07 | 37 | 63 | good (113,000) |

Example (Preparation of Composition for Producing Fiber Solution)

Example 1

Polymer compound 1 (0.50 g), 1,3,4,6-tetrakis(methoxymethyl)glycoluril (0.03 g), pyridinium p-toluenesulfonate (0.005 g), dimethylacetamide (0.49 g), and acetone (1.48 g) were mixed, and the mixture was stirred by mix rotor VMR-5 (manufactured by AS ONE Corporation) at 100 rpm until dissolution to give the composition of Example 1 for producing a fiber. The content ratio of polymer compound 1 in the composition of Example 1 for producing a fiber was about 20 wt %.

Example 2

Polymer compound 2 (0.70 g), 1,3,4,6-tetrakis(methoxymethyl)glycoluril (0.04 g), pyridinium p-toluenesulfonate (0.007 g), dimethylacetamide (0.31 g), and acetone (0.94 g) were mixed, and the mixture was stirred by mix rotor VMR-5 (manufactured by AS ONE Corporation) at 100 rpm until dissolution to give the composition of Example 2 for producing a fiber. The content ratio of polymer compound 2 in the composition of Example 2 for producing a fiber was about 35 wt %.

Example 3

Polymer compound 3 (0.23 g), 1,3,4,6-tetrakis(methoxymethyl)glycoluril (0.01 g), pyridinium p-toluenesulfonate (0.002 g), dimethylacetamide (0.50 g), and acetone (1.52 g) were mixed, and the mixture was stirred by mix rotor VMR-5 (manufactured by AS ONE Corporation) at 100 rpm until dissolution to give the composition of Example 3 for producing a fiber. The content ratio of polymer compound 3 in the composition of Example 3 for producing a fiber was about 10 wt %.

Example 4

Polymer compound 3 (0.60 g), tetrakis(methoxymethyl)glycoluril (0.03 g), pyridinium p-toluenesulfonate (0.006 g), dimethylacetamide (0.59 g), and acetone (1.77 g) were mixed, and the mixture was stirred by mix rotor VMR-5 (manufactured by AS ONE Corporation) at 100 rpm until dissolution to give the composition of Example 4 for producing a fiber. The content ratio of polymer compound 3 in the composition of Example 4 for producing a fiber was about 20 wt %.

Example 5

Polymer compound 3 (0.40 g), 1,3,4,6-tetrakis(methoxymethyl)glycoluril (0.06 g), pyridinium p-toluenesulfonate (0.004 g), dimethylacetamide (0.38 g), and acetone (1.15 g) were mixed, and the mixture was stirred by mix rotor VMR-5 (manufactured by AS ONE Corporation) at 100 rpm until dissolution to give the composition of Example 5 for producing a fiber. The content ratio of polymer compound 3 in the composition of Example 5 for producing a fiber was about 20 wt %.

Example 6

Polymer compound 4 (0.50 g), 1,3,4,6-tetrakis(methoxymethyl)glycoluril (0.03 g), pyridinium p-toluenesulfonate (0.005 g), dimethylacetamide (0.49 g), and acetone (1.48 g) were mixed, and the mixture was stirred by mix rotor VMR-5 (manufactured by AS ONE Corporation) at 100 rpm until dissolution to give the composition of Example 6 for producing a fiber. The content ratio of polymer compound 4 in the composition of Example 6 for producing a fiber was about 20 wt %.

Example 7

Polymer compound 5 (0.50 g), 1,3,4,6-tetrakis(methoxymethyl)glycoluril (0.03 g), pyridinium p-toluenesulfonate (0.005 g), dimethylacetamide (0.49 g), and acetone (1.48 g) were mixed, and the mixture was stirred by mix rotor VMR-5 (manufactured by AS ONE Corporation) at 100 rpm until dissolution to give the composition of Example 7 for producing a fiber. The content ratio of polymer compound 5 in the composition of Example 7 for producing a fiber was about 20 wt %.

Comparative Example 1

Polymer compound 3 (0.70 g), pyridinium p-toluenesulfonate (0.007 g), dimethylacetamide (0.70 g), and acetone (2.09 g) were mixed, and the mixture was stirred by mix rotor VMR-5 (manufactured by AS ONE Corporation) at 100 rpm until dissolution to give the composition of Comparative Example 1 for producing a fiber. The content ratio of polymer compound 3 in the composition of Comparative Example 1 for producing a fiber was about 20 wt %.

Comparative Example 2

Polymer compound 3 (0.70 g), 1,3,4,6-tetrakis(methoxymethyl)glycoluril (0.035 g), dimethylacetamide (0.69 g), and acetone (2.07 g) were mixed, and the mixture was stirred by mix rotor VMR-5 (manufactured by AS ONE Corporation) at 100 rpm until dissolution to give the composition of Comparative Example 2 for producing a fiber. The content ratio of polymer compound 3 in the composition of Comparative Example 2 for producing a fiber was about 20 wt %.

Comparative Example 3

Polymer compound 3 (0.70 g), dimethylacetamide (0.70 g), and acetone (2.10 g) were mixed, and the mixture was stirred by mix rotor VMR-5 (manufactured by AS ONE Corporation) at 100 rpm until dissolution to give the composition of Comparative Example 3 for producing a fiber. The content ratio of polymer compound 3 in the composition of Comparative Example 3 for producing a fiber was about 20 wt %.

Comparative Example 4

Polymer compound 6 (0.26 g), pyridinium p-toluenesulfonate (0.003 g), dimethylacetamide (1.70 g), and acetone (0.96 g) were mixed, and the mixture was stirred by mix rotor VMR-5 (manufactured by AS ONE Corporation) at 100 rpm until dissolution to give the composition of Comparative Example 4 for producing a fiber. The content ratio of polymer compound 6 in the composition of Comparative Example 4 for producing a fiber was about 8.9 wt %.

The constitutions of the compositions of Examples 1-7, and Comparative Examples 1-4 for producing a fiber are shown in Tables 2-1 and 2-2.

mm (manufactured by Musashi engineering) was attached. The distance from the needle tip to the substrate for receiving the fiber (discharge distance) was set to 20 cm. The applied voltage was 25 kV, and the discharge speed was 10 μl/min.

[Confirmation Method of Fiber Form]

In the following Experimental Examples 1-4, the fiber form was confirmed by vapor depositing Pt—Pd on the fiber for 1 min by ion sputter (E-1030, manufactured by Hitachi High-Technologies Corporation), and observing same under a scanning electron microscope (SEM) (S-4800, manufactured by Hitachi High-Technologies Corporation) at magnification ×10,000.

When the fiber form was maintained, "good" is indicated, and when the fiber form was not maintained, "not good" is indicated.

[Measurement Method of Fiber Diameter]

In the following Experimental Examples 1-4, the fiber diameter (thickness of fiber) was measured using a scanning

TABLE 2-1

| | polymer compound (component A) | weight average molecular weight of component A | content ratio (wt %) of component A | crosslinking agent (component B) | content ratio (wt %) of component B | acid compound (component C) | solvent (component D) |
|---|---|---|---|---|---|---|---|
| Example 1 | 1 | 217000 | 20.0 | PL-LI | 1.2 | PyPTS | DMAc/acetone |
| Example 2 | 2 | 13000 | 35.1 | PL-LI | 2.0 | PyPTS | DMAc/acetone |
| Example 3 | 3 | 182000 | 10.2 | PL-LI | 0.44 | PyPTS | DMAc/acetone |
| Example 4 | 3 | 182000 | 20.0 | PL-LI | 1.0 | PyPTS | DMAc/acetone |
| Example 5 | 3 | 182000 | 20.1 | PL-LI | 3.0 | PyPTS | DMAc/acetone |
| Example 6 | 4 | 265000 | 20.0 | PL-LI | 1.2 | PyPTS | DMAc/acetone |
| Example 7 | 5 | 113000 | 20.0 | PL-LI | 1.2 | PyPTS | DMAc/acetone |

TABLE 2-2

| | polymer compound | weight average molecular weight of polymer compound | content ratio (wt %) of polymer compound | crosslinking agent (component B) | content ratio (wt %) of component B | acid compound (component C) | solvent (component D) |
|---|---|---|---|---|---|---|---|
| Comparative Example 1 | 3 | 182000 | 20.0 | — | — | PyPTS | DMAc/acetone |
| Comparative Example 2 | 3 | 182000 | 20.0 | PL-LI | 1.0 | — | DMAc/acetone |
| Comparative Example 3 | 3 | 182000 | 20.0 | — | — | — | DMAc/acetone |
| Comparative Example 4 | 6 | 230000 | 8.9 | — | — | PyPTS | DMAc/acetone |

Note) PL-LI: 1,3,4,6-tetrakis(methoxymethyl)glycoluril, PyPTS: pyridinium p-toluenesulfonate, DMAc: dimethylacetamide

[Production of Fiber by Electrospinning Method]

In the following Experimental Examples 1-4, fibers were produced by an electrospinning method by using Esprayer ES-2000 (manufactured by Fuence Co., Ltd.). The composition for producing a fiber was filled in a 1 ml lock-type glass syringe (manufactured by AS ONE Corporation), and a lock-type metallic needle 24G with needle length of 13 electron microscope (SEM) (S-4800, manufactured by Hitachi High-Technologies Corporation), by taking and preserving images at magnification ×10,000 and measuring by the attached length measuring tool.

Experimental Example 1: Heat Treatment and Solvent Resistance Test

The compositions of Examples 1-7 and Comparative Examples 1-4 for producing a fiber were spun on aluminum foil by an electrospinning method immediately after preparation. The obtained fibers were subjected to a heat treatment under conditions shown in Table 3, and the fiber form after the heat treatment was confirmed. The results are shown in Table 3.

The compositions of Examples 1-7 and Comparative Examples 1-4 for producing a fiber were spun on aluminum foil by an electrospinning method immediately after preparation. The obtained fibers were subjected to a heat treatment under conditions shown in Table 4. The fibers were immersed in ethanol for 10 sec, the fiber form was confirmed again, and the fiber diameter was measured. The results are shown in Table 4.

The compositions of Example 4 and Comparative Examples 1-3 for producing a fiber were spun on aluminum foil by an electrospinning method immediately after preparation. The obtained fibers were subjected to a heat treatment under conditions shown in Table 5. The fibers were immersed in a liquid medium, ISCOVE'S MODIFIED DULBECCO'S MEDIUM (manufactured by Sigma Ltd.) for 7 days, washed with water and with ethanol, the fiber form was confirmed again and the fiber diameter was measured. The results are shown in Table 5.

TABLE 3

(fiber form after heat treatment)

| | temperature | | |
|---|---|---|---|
| | 80° C. | 180° C. | |
| time | 24 hr | 10 min | 30 min |
| Example 1 | — | good | good |
| Example 2 | — | good | — |
| Example 3 | — | — | good |
| Example 4 | good | good | good |
| Example 5 | good | — | — |
| Example 6 | — | good | — |
| Example 7 | — | good | — |
| Comparative Example 1 | good | good | — |
| Comparative Example 2 | good | good | — |
| Comparative Example 3 | good | good | — |
| Comparative Example 4 | — | good | — |

TABLE 4

(fiber form and fiber diameter after heat treatment → ethanol immersion)

| | temperature | | |
|---|---|---|---|
| | 80° C. | 180° C. | |
| time | 24 hr | 10 min | 30 min |
| Example 1 | — | good (about 400 nm) | good (about 430 nm) |
| Example 2 | — | good (about 220 nm) | — |
| Example 3 | — | — | good (about 70 nm) |
| Example 4 | good (about 460 nm) | good (about 500 nm) | good (about 450 nm) |
| Example 5 | good (about 470 nm) | — | — |
| Example 6 | — | good (about 510 nm) | — |
| Example 7 | — | good (80-750 nm) | — |
| Comparative Example 1 | fiber form retained rough fiber surface | good (about 770 nm) | — |
| Comparative Example 2 | fiber form retained rough fiber surface | good (about 400 nm) | — |
| Comparative Example 3 | fiber flaking | fiber form retained rough fiber surface | — |
| Comparative Example 4 | — | good (about 440 nm) | — |

TABLE 5

(fiber form and fiber diameter after heat treatment → liquid medium immersion)

| | temperature | | |
|---|---|---|---|
| | 80° C. | 180° C. | |
| time | 24 hr | 10 min | 30 min |
| Example 4 | good (about 420 nm) | — | good (about 540 nm) |
| Comparative Example 1 | mesh form | mesh form | — |
| Comparative Example 2 | mesh form | fiber flaking | — |
| Comparative Example 3 | fiber flaking | fiber flaking | — |

(fiber flaking; formed fiber becomes flakes and disappears from aluminum foil)

From the results of Table 3, the fibers produced using the compositions of Examples 1-7 and Comparative Examples 1-4 for producing a fiber and by an electrospinning method, and subjected to a heat treatment alone showed a good form irrespective of the NSuMA/HPMA composition ratio, the molecular weight of polymer compound and the content of polymer compound, and the content of crosslinking agent.

From the results of Table 4, the fibers produced using the compositions of Examples 1-7 for producing a fiber and subjected to a heat treatment showed a good form even after further immersion in ethanol for 10 sec. While a good fiber form was found in Example 7, a wide range of fiber diameter was observed. Furthermore, the results of Example 4 and Example 5 showed a good fiber form, even when the heating temperature in the heat treatment was 80° C.

From the results of Table 5, the fiber produced using the composition of Example 4 for producing a fiber showed a good form even after immersion in a liquid medium for cell culture for 7 days.

In other words, when the composition for producing a fiber of the present invention is spun to produce a fiber, a heat treatment at not less than 80° C. is more desirable to provide a fiber showing good fiber form, and superior in organic solvent resistance and medium resistance.

Also, it was suggested that, when electrospinning is performed under the above-mentioned conditions, the diameter of the produced fiber depends on the weight average molecular weight of the polymer compound of component A, and the content ratio of the polymer compound of component A in the composition for producing a fiber. Therefore, a fiber having a desired fiber diameter can be obtained by adjusting the weight average molecular weight of the polymer compound of component A, and the content ratio of the polymer compound of component A in the composition for producing a fiber.

Experimental Example 2: Cell Culture Evaluation 1

The compositions of Example 1 and Comparative Example 4 for producing a fiber were spun by an electrospinning method, and cell culture on the obtained fiber was evaluated. In the following, the $CO_2$ concentration (%) of $CO_2$ incubator is shown in % by volume of $CO_2$ in the atmosphere.

[Production of Fiber of Example 1]

The composition of Example 1 for producing a fiber was spun by an electrospinning method, blown against a glass substrate for 20 min and heat treated at 180° C. for 30 min. As the glass substrate, microcover glass (manufactured by Matsunami Glass Ind., Ltd.) (Ф32 mm, thickness about 0.5 mm) was used. The obtained fiber was washed with ethanol and air dried, and the fiber form was confirmed under a scanning electron microscope (SEM). The fiber diameter of the fiber obtained from the composition of Example 1 for producing a fiber was about 430 nm.

In the following, the glass substrate on which the composition of Example 1 for producing a fiber was spun to form a fiber is conveniently referred to as "the fiber substrate of Example 1".

[Production of Fiber of Comparative Example 4]

The composition of Comparative Example 4 for producing a fiber was spun by an electrospinning method, blown against a glass substrate for 20 min and heat treated at 180° C. for 10 min. As the glass substrate, microcover glass (manufactured by Matsunami Glass Ind., Ltd.) (Ф32 mm, thickness about 0.5 mm) was used. The obtained fiber was washed with ethanol and air dried, and the fiber form was confirmed under a scanning electron microscope (SEM). The fiber diameter of the fiber obtained from the composition of Comparative Example 4 for producing a fiber was about 440 nm.

In the following, the glass substrate on which the composition of Comparative Example 4 for producing a fiber was spun to form a fiber is conveniently referred to as "the fiber substrate of Comparative Example 4".

[Preparation of Cell]

As the cell, human embryonic kidney cell line Hek293 (manufactured by DS Pharma Biomedical Co., Ltd.) was used. The medium used for cell culture was EMEM (Eagle's Minimum Essential Medium) medium (manufactured by Wako Pure Chemical Industries, Ltd.) containing 10% (v/v) FBS and 1% (v/v) NEAA (Non-Essential Amino Acids) (manufactured by GIBCO). The cells were subjected to standing culture using a diameter 10 cm petri dish (medium 10 mL) for 2 days or longer in a $CO_2$ incubator at 37° C. while maintaining 5% carbon dioxide concentration. The cells were washed with PBS (10 mL), trypsin-EDTA (ethylenediaminetetraacetic acid) solution (manufactured by Wako Pure Chemical Industries, Ltd.) (1 mL) was added to detach the cells, which were suspended in the above-mentioned medium (10 mL). The suspension was centrifuged (manufactured by TOMY SEIKO Co., Ltd., LC-200, 1000 rpm/3 min, room temperature), the supernatant was removed, and the above-mentioned medium was added to prepare a cell suspension. PBS means phosphate buffered saline (manufactured by Sigma-Aldrich Japan), FBS means fetal calf serum (manufactured by Biological Industries).

[Sterilization of Substrate]

The fiber substrate of Example 1, the fiber substrate of Comparative Example 4, and an untreated glass substrate as a control were disposed on a 6 well flat-bottom microplate (manufactured by AS ONE Corporation), 70% ethanol (2 mL) was added to immerse the plate at room temperature for 5 min, and the plate was air dried.

[Immobilization of Cell Adhesion Substance]

The fiber substrate of Example 1 was disposed on a 6 well flat-bottom microplate, 70% ethanol (2 mL) was added to immerse the plate at room temperature for 5 min. The solution was removed, and the plate was air dried. Laminin 521 (manufactured by BioLamina)/PBS solution (20 μg/mL) was added at 2 mL per 1 well. The mixture was stood in an incubator at 37° C. for 2 hr to immobilize laminin. The solution was removed, and the plate was washed twice with 2 mL of PBS per 1 well.

[Cell Culture]

The sterilized fiber substrate of Example 1, the fiber substrate of Comparative Example 4, an untreated glass substrate, and the fiber substrate of Example 1, on which laminin 521 was immobilized, were disposed on a 6 well flat-bottom microplate, and washed twice with a medium (2 mL). Thereafter, a cell suspension of Hek293 (human embryonic kidney cell) prepared to $2.0 \times 10^5$ cells/well was added at 2 mL each. Thereafter, the microplate was stood in a $CO_2$ incubator at 37° C. for 24 hr while maintaining 5% carbon dioxide concentration.

[Cell number count using WST-8]

After cell culture for 24 hr, the supernatant on each fiber substrate, and untreated glass substrate (control) was removed, and the cells were washed with PBS (2 mL). PBS was removed, 1 mL of EMEM medium containing 10% (v/v) FBS and 1% (v/v) NEAA (manufactured by GIBCO) was added, and 100 μL of WST-8 reagent (manufactured by KISHIDA CHEMICAL Co., Ltd.) was added. After standing in a $CO_2$ incubator at 37° C. for 100 min, the reaction solution (100 μL) was transferred to a 96 well flat-bottom microplate, and the absorbance at 450 nm was measured by an absorption spectrometer (manufactured by Molecular Devices, SpectraMax).

The results of each cell number measurement are shown Table 6 (mean of n=2).

TABLE 6

| | absorbance (450 nm) (WST-8) |
|---|---|
| fiber substrate of Example 1 immobilized with Laminin 521 | 0.31 |
| fiber substrate of Example 1 | 0.18 |
| fiber substrate of Comparative Example 4 | 0.14 |
| glass substrate | 0.16 |

From the results of Table 6, it was found that HEK293 cells grow on the fiber substrate of Example 1 heated at 180° C., by which it was shown that the fiber produced using the composition of Example 1 for producing a fiber is harmless on living organisms. In addition, the cell proliferation ratio was improved by about 2-fold on the fiber substrate of Example 1 immobilized with laminin 521. Therefrom it was clarified that the fiber of the present invention immobilized with a substance effective for cell culture improves cell proliferation.

Experimental Example 3: Cell Culture Evaluation 2

The composition of Example 5 for producing a fiber was spun by an electrospinning method, and cell culture on the obtained fiber was evaluated. The cell culture method was performed according to Experimental Example 2.

[Production of Fiber of Example 5]

The composition of Example 5 for producing a fiber was spun by an electrospinning method, blown against a Φ30 mm polystyrene (PS) substrate for 20 min and heat treated at 80° C. for 24 hr. The Φ30 mm PS substrate was self-produced from "PLABAN" (trade name; thickness 0.2 mm) manufactured by ACRYSUNDAY Co., Ltd. The obtained fiber was washed with ethanol and air dried, and the fiber form was confirmed under a scanning electron microscope (SEM). The fiber diameter of the fiber obtained from the composition of Example 5 for producing a fiber was about 470 nm.

In the following, the PS substrate on which the composition of Example 5 for forming a fiber was spun to produce a fiber is conveniently referred to as "the fiber substrate of Example 5".

[Immobilization of Cell Adhesion Substance]

The fiber substrate of Example 5 was disposed on a 6 well flat-bottom microplate, YIGSR peptide (manufactured by BEX Co., Ltd.)/PBS solution (0.05 wt %) was added at 2 mL per 1 well. The plate was stood at room temperature for 24 hr to immobilize peptide. The solution was removed, and the plate was washed twice with 2 mL of PBS per 1 well.

[Sterilization of substrate]

The fiber substrate of Example 5, the fiber substrate of Example 5 on which peptide was immobilized, and an untreated PS substrate as a control were disposed on a 6 well flat-bottom microplate (manufactured by AS ONE Corporation), 70% ethanol (2 mL) was added to immerse the plate at room temperature for 5 min, and the plate was air dried.

[Cell Culture]

The sterilized fiber substrate of Example 5, fiber substrate of Example 5 on which peptide was immobilized, and untreated PS substrate as a control were disposed on a 6 well flat-bottom microplate, and washed twice with a medium (2 mL). Thereafter, a cell suspension of Hek293 (human embryonic kidney cell) prepared to $2.0 \times 10^5$ cells/well was added at 2 mL each. Thereafter, the microplate was stood in a $CO_2$ incubator at 37° C. for 24 hr while maintaining 5% carbon dioxide concentration.

[Cell Number Count Using WST-8]

After cell culture for 24 hr, the supernatant on the fiber substrate of Example 5, fiber substrate of Example 5 on which peptide was immobilized, and untreated PS substrate (control) used for the cell culture were removed, and the cells were washed with PBS (2 mL). PBS was removed, 1 mL of EMEM medium containing 10% (v/v) FBS and 1% (v/v) NEAA (manufactured by GIBCO) was added, and 100 μL of WST-8 reagent (manufactured by KISHIDA CHEMICAL Co., Ltd.) was added. After standing in a $CO_2$ incubator at 37° C. for 100 min, the reaction solution (100 μL) was transferred to a 96 well flat-bottom microplate, and the absorbance at 450 nm was measured by an absorption spectrometer (manufactured by Molecular Devices, SpectraMax).

The results of each cell number measurement are shown Table 7 (mean of n=2).

TABLE 7

| | absorbance (450 nm) (WST-8) |
|---|---|
| fiber substrate of Example 5 immobilized with peptide | 0.40 |
| fiber substrate of Example 5 | 0.25 |
| PS substrate | 0.10 |

From the results of Table 7, it was found that Hek 293 cells grew more by 2.5-fold on the fiber substrate of Example 5 as compared to the untreated PS substrate. The cells grew more by 4.0-fold on the fiber substrate of Example 5 on which peptide was immobilized. Therefrom it was clarified that the fiber of the present invention has cell proliferation property and the fiber of the present invention immobilized with a substance effective for cell culture improves cell proliferation.

Experimental Example 4: Cell Culture Evaluation 3

The compositions of Example 4 and Comparative Example 4 for producing a fiber were spun by an electrospinning method, and cell culture was evaluated on the obtained fibers. In the following, the concentration (%) of $CO_2$ of the $CO_2$ incubator shows % by volume of $CO_2$ in the atmosphere.

[Production of Fiber of Example 4]

The composition of Example 4 for producing a fiber was spun by an electrospinning method, blown against a glass substrate for 20 min and heat treated at 180° C. for 30 min. As the glass substrate, microcover glass (manufactured by Matsunami Glass Ind., Ltd.) (Φ32 mm, thickness about 0.5 mm) was used. The obtained fiber was washed with ethanol and air dried, and the fiber form was confirmed under a scanning electron microscope (SEM). The fiber diameter of the fiber obtained from the composition of Example 4 for producing a fiber was about 440 nm.

In the following, the glass substrate on which the composition of Example 4 for producing a fiber was spun to form a fiber is conveniently referred to as "the fiber substrate of Example 4".

[Production of Fiber of Comparative Example 4]

The composition of Comparative Example 4 for producing a fiber was spun by an electrospinning method, blown against a glass substrate for 20 min and heat treated at 180° C. for 10 min. As the glass substrate, microcover glass (manufactured by Matsunami Glass Ind., Ltd.) (Φ32 mm, thickness about 0.5 mm) was used. The obtained fiber was washed with ethanol and air dried, and the fiber form was confirmed under a scanning electron microscope (SEM). The fiber diameter of the fiber obtained from the composition of Comparative Example 4 for producing a fiber was about 440 nm.

In the following, the glass substrate on which the composition of Comparative Example 4 for producing a fiber was spun to form a fiber is conveniently referred to as "the fiber substrate of Comparative Example 4".

[Cell Preparation]

Mouse fibroblast (MEF; harvested and adjusted from E12.5 ICR mouse manufactured by Japan SLC, Inc.) or human ES cell (H9 strain) or human iPS cell (253G1 strain) cultured on Matrigel human ESC-qualified matrix (manufactured by Corning) was washed twice with D-PBS(−) (manufactured by Life technologies), TrypLE Express (1 mL) was added and the mixture was stood at 37° C. for 5 min. TrypLE Express was removed by suction, and the cells were recovered from mTeSR1 (manufactured by VERITAS Corporation) (hereinafter mTeSR1/10 μM Y27632) medium containing Y-27632 (manufactured by Wako Pure Chemical Industries, Ltd.) at a final concentration of 10 μM. The cell suspension was pipetted into single cells, and centrifuged at rotation number 1000 rpm/3 min at room temperature. The supernatant was removed, and the cell pellets were suspended again in mTeSR1/10 μM Y27632 medium, and the cell number was measured by NucleoCounter NC-200 (hereinafter NC-200; manufactured by ChemoMetecAS).

[Sterilization of Substrate]

The fiber substrate of Example 4, and the fiber substrate of Comparative Example 4 were disposed on a 6 well flat-bottom microplate (manufactured by BD Bioscience), washed 3 times with 100% ethanol (1 mL), and air dried. Thereafter, the cells were washed 3 times with Dulbecco's Modified Eagle Medium: Nutrient Mixture F-12 (DMEM/F-12; manufactured by Sigma Aldrich) solution (1 mL).

[Immobilization of Cell Adhesion Substance]

The fiber substrate of Example 4 and an untreated glass substrate were disposed on a 6 well flat-bottom microplate (manufactured by BD Bioscience), and washed 3 times with 100% ethanol (1 mL), air-dried, and washed 3 times with D-PBS(−) or DMEM/F-12 solution (1 mL). To the fiber substrate of Example 4 was added 1 mL of laminin 511 (manufactured by BioLamina) solution prepared with D-PBS(−) to a final concentration of 100 μg/10 mL, and the substrate was stood at 37° C. for 2 hr or at 4° C. overnight and washed once with DMEM/F-12 solution (1 mL). To the glass substrate was added 1 mL of Matrigel solution diluted 75-fold with DMEM/F-12, and the substrate was stood at 37° C. for 2 hr or at 4° C. overnight and washed once with DMEM/F-solution (1 mL).

[Cell Culture]

The sterilized fiber substrate of Example 4, sterilized fiber substrate of Comparative Example 4, the fiber substrate of Example 4 on which laminin 511 was immobilized, and glass substrate coated with Matrigel (manufactured by Corning Incorporated) were disposed on a 6 well flat-bottom microplate (manufactured by BD Bioscience), and a suspension of human ES cell or human iPS cell was added at 1.5-2.0×10$^5$ cells/well. After 37° C. for 24 hr (day 1 of culture), the medium was exchanged with mTeSR1/10 μM Y27632 medium (1.5 mL). On day 2 to day 4 of culture, the medium was exchanged with mTeSR1 medium (1.5 mL). During the culture period, the cells were stood at 37° C. in a $CO_2$ incubator while maintaining 5% carbon dioxide concentration.

[Cell Number Count]

After 4 days of culture, the medium was removed, and the cell layer was washed with D-PBS(−). Then, TrypLE Express (0.5 mL) was added, and the mixture was stood at 37° C. for 1 min or 3 min. The cells were recovered, centrifuged at rotation number 1000 rpm/3 min, and the supernatant was removed. The cell pellets were suspended in DMEM/F-12 solution again, and the cell number and survival rate were measured by NC-200. The cell proliferation efficiency was calculated by cell number on day 4 of culture/seeded cell number.

The results of proliferation efficiency of each cell are shown Table 8 (human ES cell) and Table 9 (human iPS cell) (mean of n=2).

TABLE 8

|  | human ES cell proliferation efficiency | human ES cell survival rate (%) |
|---|---|---|
| fiber substrate of Example 4 immobilized with laminin 511 | 6.65 | 95.3 |
| fiber substrate of Example 4 | 2.87 | 93.3 |
| fiber substrate of Comparative Example 4 | 0.38 | 90.7 |
| glass substrate coated with Matrigel | 7.20 | 95.1 |

TABLE 9

|  | human iPS cell proliferation efficiency | human iPS cell survival rate (%) |
|---|---|---|
| fiber substrate of Example 4 immobilized with laminin 511 | 3.87 | 88.0 |
| fiber substrate of Example 4 | 0.10 | 83.3 |
| fiber substrate of Comparative Example 4 | undetectable | undetectable |
| glass substrate coated with Matrigel | 4.18 | 68.8 |

From the results of Table 8 and Table 9, it was found that the fiber substrate of Example 4 is effective for the culture of human ES cell and human iPS cell than the fiber substrate of Comparative Example 4. In addition, it was found that the cell proliferation rate of the fiber substrate of Example 4 immobilized with laminin 511 is of the same level as the cell proliferation rate of the glass substrate coated with Matrigel, from which it was clarified that immobilization of a cell adhesion substance on a fiber substrate is effective for cell culture.

Furthermore, from the results of human iPS cell survival rate in Table 9, the cell survival rate of the fiber substrate of Example 4 immobilized with laminin 511, and the fiber substrate of Example 4 was about 20% higher than the glass substrate coated with Matrigel. The results reveal that the fiber of the present invention is effective for cell culture.

INDUSTRIAL APPLICABILITY

According to the present invention, a composition for producing a fiber, which is preferable for immobilizing substances effective for cell adhesion•proliferation•differentiation and the like, and retains organic solvent resistance, a fiber obtained by spinning the composition, and a cell culture scaffold material using the fiber can be provided. Such fiber expresses a more superior function as a cell culture scaffold material by immobilizing substances effective for cell adhesion•proliferation•differentiation and the like.

This application is based on patent application No. 2014-027044 filed in Japan (filing date: Feb. 14, 2014), the contents of which are encompassed in full herein.

The invention claimed is:

1. A composition for producing a fiber, comprising
   (A) a polymer compound comprising a unit structure represented by the formula (1) and a unit structure represented by the formula (2),
   (B) a crosslinking agent,
   (C) an acid compound that promotes a crosslinking reaction of hydroxyl groups of polymer compound (A) with crosslinking agent (B), and
   (D) a solvent

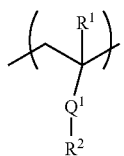

(1)

wherein
$R^1$ is a hydrogen atom or a methyl group,
$Q^1$ is an ester bond or amide bond,
$R^2$ is an alkyl group having 1-10 carbon atoms or an aromatic hydrocarbon group having 6-10 carbon atoms, wherein at least one hydrogen atom is substituted by a hydroxy group,

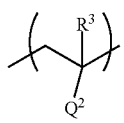

(2)

wherein
$R^3$ is a hydrogen atom or a methyl group, and
$Q^2$ is an active ester group.

2. The composition according to claim 1, wherein the above-mentioned $Q^2$ is represented by the formula (5):

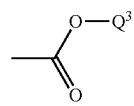

(5)

wherein $Q^3$ is an N-succinimide group, a p-nitrophenyl group or a pentafluorophenyl group.

3. The composition according to claim 1, wherein the above-mentioned polymer compound has a weight average molecular weight of 1,000-1,000,000.

4. The composition according to claim 1, wherein the above-mentioned solvent is a polar solvent.

5. A production method of a fiber, comprising a step of spinning the composition according to claim 1 to produce a spun fiber.

6. The method according to claim 5, wherein the above-mentioned spinning is electrospinning.

7. The method according to claim 5, comprising a step of heating the spun fiber at 70-300° C.

8. The method according to claim 5, further comprising a step for immobilizing a cell adhesion substance on the fiber by reaction between the active ester group in the fiber and the cell adhesion substance.

9. A fiber produced by the method according to claim 5.

10. A cell culture scaffold material comprising the fiber according to claim 9.

\* \* \* \* \*